Figure 1:
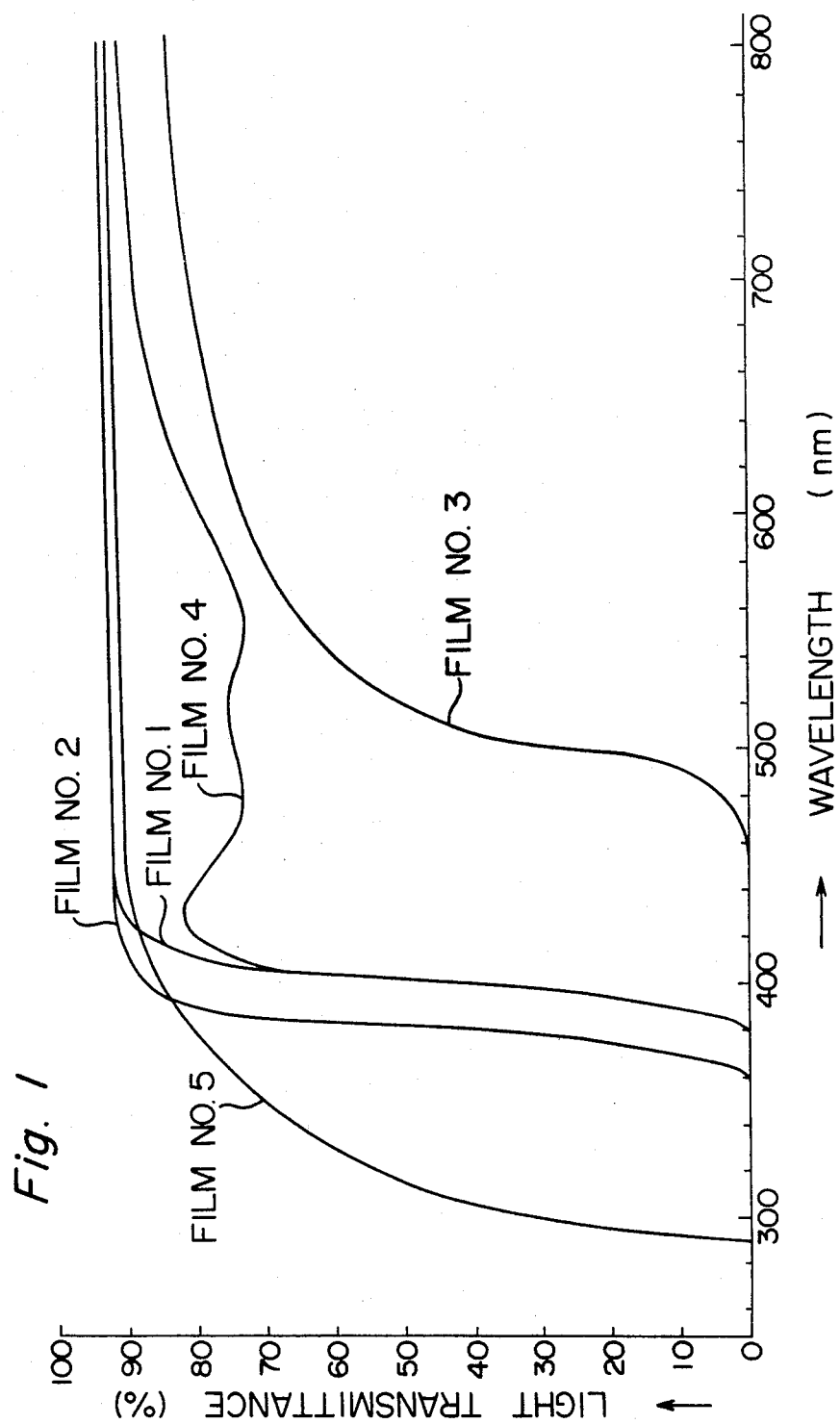

United States Patent [19]

Harasawa et al.

[11] 4,235,043
[45] Nov. 25, 1980

[54] METHOD FOR CULTIVATING ALGAE AND A COVERING MATERIAL USED THEREFOR

[75] Inventors: Isamu Harasawa, Kiyose; Yukio Hariki, Funabashi; Katsuhiko Maeda; Kouichi Nakamura, both of Uozu, all of Japan

[73] Assignee: Nippon Carbide Kogyo Kabashiki Kaisha, Tokyo, Japan

[21] Appl. No.: 20,507

[22] Filed: Mar. 14, 1979

[30] Foreign Application Priority Data

Oct. 28, 1978 [JP] Japan .................................. 53-132116

[51] Int. Cl.³ .............................................. A01G 7/00
[52] U.S. Cl. .......................................... 47/1.4; 47/17; 47/DIG. 6
[58] Field of Search ...................... 47/1.4, DIG. 6, 58, 47/17

[56] References Cited

U.S. PATENT DOCUMENTS

| | | | |
|---|---|---|---|
| 3,043,709 | 7/1962 | Amborski | 47/17 X |
| 3,403,471 | 10/1968 | Clement et al. | 47/1.4 |
| 3,542,710 | 11/1970 | Glatti | 47/17 X |
| 3,879,890 | 4/1975 | Chen et al. | 47/1.4 |
| 4,084,346 | 4/1978 | Stengel et al. | 47/1.4 |
| 4,087,936 | 5/1978 | Savins et al. | 47/1.4 |

OTHER PUBLICATIONS

The Algae: A Review, Prescott, 1968, Houghton Miffton Co., pp. 311-312.

*Primary Examiner*—Robert E. Bagwill
*Attorney, Agent, or Firm*—Sherman & Shalloway

[57] ABSTRACT

A method for cultivating an alga, which comprises growing the alga in a light field substantially free from light of wavelengths of not more than 340 nm; and a covering material for use in the cultivation of algae, said covering material substantially inhibiting the transmission of light of wavelengths of not more than 340 nm.

9 Claims, 2 Drawing Figures

METHOD FOR CULTIVATING ALGAE AND A COVERING MATERIAL USED THEREFOR

This invention relates to the cultivation of algae. More specifically, it pertains to a method for cultivating algae which promotes the growth of the algae, and affords the algae of improved quality in increased yields, and to a covering material used in this method.

With a worldwide increase in population in recent years, the problem of food shortage has come to the fore. Since cultivation of terrestrial plants is limited, much interest has been aroused in the cultivation of algae as one means of overcoming the food shortage. Resources for the algae are abundant, and there is a great possibility of their mass-production by artificial means. Some algae, such as Chlorella, Spirulina, and Scenedesmus, have already been cultivated on a commercial basis. These algae are produced by cultivation in outdoor pools, or in tanks. The former outdoor cultivation has the defect that it is restricted in place, the output is affected by weather, and the quality of the cultivated algae varies according to such conditions as the place of cultivation and weather. The latter method of tank cultivation also has the defect that a large-sized equipment is required, and since artificial light rays are used, the output is low and the quality of the algae is not entirely satisfactory.

Seaweeds such as laver (genus Porphyra such as P. tenera), genus Laminaria (e.g., *Laminaria japonica*) and genus Undaria (e.g., *Undaria pinnetifida*) are cultivated in some parts of the world for human consumption, but no sufficient improvement in the yield and quality of these seaweeds has been achieved.

In order to cultivate algae which are regarded as important food sources, the present inventors have made investigations about the promotion of algal growth, the increase of the yield of the algae and the improvement of their quality in connection with light-irradiating conditions. These investigations have led to the surprising discovery that when algae are cultivated in a light field substantially free from light of wavelengths of not more than 340 nm, the growth of the algae is promoted, and in some types of algae, their qualities such as appearance, flavor and softness to the palate can be markedly improved.

Thus, according to this invention, there is provided a method for cultivating algae which comprises growing the algae in a light field substantially free from light of wavelengths of not more than 340 nm.

The algae to which the method of this invention can be applied denote a kind of Cryptogamae plants which, whether one-celled or complex-structured, produce reproductive organs which, in principle, are always one-celled, bear chlorophyll, and perform photosynthesis. In taxonomy, the algae comprise eight divisions of the plant kingdom: Cyanophyta, or blue-green algae; Rhodophyta, or red algae; Chrysophyta, or yellow-green algae; Pyrrhophyta, or dinoflagellates; Phaeophyta, or brown algae; Euglenophyta; Chlorophyta, or green algae; and Charophyta.

Generally, the method of this invention can be applied to algae of any of these divisions, whether they are unicellular algae or huge algae, to achieve varying degrees of growth promotion, increased output, and/or improved quality. These effects are especially outstanding when the method is applied to algae of the divisions Cyanophyta, Rhodophyta, Chrysophyta, Phaeophyta, and Chlorophta.

Examples of typical algae to which the method of this invention can be applied are shown below. In the following list, typical examples of species are shown in the parentheses after the indication of genera.

[1] Division Cyanophyta

A. Class Cyanophyceae

A-1.
Order Chroococcales
A-1-1.
Family Chroococcaceae
Genus Anacystis (*A. nidulance*),
Genus Aphanocapsa Nägeli (*A. pulchra*),
Genus Aphanothece Nägeli (*A. sacrum*),
Genus Chroococcus Nägeli (*C. turgidus*),
Genus Coelosphaerium Nägeli,
Genus Glaucocystis Itzigsohn (*G. nostochinearum*),
Genus Gloeocapsa Kützing,
Genus Gloeochaete Lagerheim (*G. wittrockiana*),
Genus Gloeothece Nägeli (*G. linearis*),
Genus Gomphosphaeria Kützing (*G. aponina*),
Genus Merismopedia Meyen (*M. elegans*),
Genus Microcystis Kützning (*M. aeruginosa*),
Genus Synechococcus Nägeli (*S. aeruginosus*), and
Genus Synechocystis Sauvageau (*S. aquatilis*).
A-1-2.
Family Entophysalidaceae
Genus Chlorogloea Wille, and
Genus Entophysalis Kützing.
A-2.
Order Chamaesiphonales
A-2-1.
Family Dermocarpaceae
Genus Dermocarpa Grouan.
A-2-2.
Family Chamaesiphonaceae
Genus Chamaesiphon A. Braun et Grunow (*C. incrustans*).
A-2-3.
Family Siphononemaceae
Genus Siphononema Geitler.
A-3.
Order Pleurocapsales
A-3-1.
Family Pleurocapsaceae
Genus Pleurocapsa Thuret et Hauck, and
Genus Xenococcus Thuret.
A-3-2.
Family Hyellaceae
Genus Hydrococcus Kützing, and
Genus Hyella Bornet.
A-4.
Order Nostocales
A-4-1.
Family Oscillatoriaceae
Genus Arthrospira Stizenverger (*A. juneri*),
Genus Gomontiella Teodoresco,
Genus Lyngbya Agardh (*L. contorta*),
Genus Microcoleus Desmazieres (*M. vaginatus*),
Genus Oscillatoria Vaucher (*O. formosa*),
Genus Phormidium Kützing (*P. autumnale*),
Genus Porphyrosiphon Kützing,
Genus Schizothrix Kützing (*S. purpurascens*),
Genus Spirulina Turpin (*S. princeps*),
Genus Symploca Kützing (*S. muscorum*), and Genus Trichodesmium Ehrenberg (*T. lacustre*).
A-4-2.
  Family Nostocaceae
  Genus Anabaena Bory (*A. spiroides*),
  Genus Anabaenopsis Woloszynska (*A. arnordii*),
  Genus Aphanizomenon Morren (*A. flos-aquae*),
  Genus Cylindrospermum Kützing (*C. muscicola*),
  Genus Nodularia Martens (*N. spumigena*),
  Genus Nostoc Vaucher (*N. verr cosum, N. commune, N. commune* var. *flagelliforme*), and
  Genus Wollea Bornet et Flahault.
A-4-3.
  Family Microchaetaceae
  Genus Microchaete Thuret.
A-4-4.
  Family Rivulariaceae
  Genus Amphithrix Kützing,
  Genus Calothrix Agardh (*C. braunii*),
  Genus Dichothrix Zanardini,
  Genus Gloeotrichia Agardh,
  Genus Raphidiopsis Fritsch et Rich, and
  Genus Rivularia Roth (*R. globiceps*).
A-4-5.
  Family Scytonemataceae
  Genus Plectonema Thuret,
  Genus Scytonema Agardh, and
  Genus Tolypothrix Kützing.
A-4-6.
  Family Brachytrichiaceae
  Genus Brachytrichia Zanardini.
A-5.
  Order Stigonematales
A-5-1.
  Family Pulvinulariaceae
  Genus Pulvinularia Borzi.
A-5-2.
  Family Capsosiraceae
  Genus Capsosira (*C. brebissonii*).
A-5-3.
  Family Nostochopsidaceae
  Genus Mastigocoleus Lagerheim,
  Genus Nostochopsis Wood (*N. wichmannii*).
A-5-4.
  Family Stigonemataceae
  Genus Fischerella Gomont (*F. major*),
  Genus Hapalosiphon Nägeli (*H. intricatus*),
  Genus Mastigocladus Chon (*M. laminosus*),
  Genus Stigonema Agardh (*S. ocellatum*), and
  Genus Westiella Borzi.

In the division Cyanophyta, algaes belonging to the genera Aphanocapsa, Aphanothece, Anacystis, Microcystis, Oscillatoria, Spirulina, Anabaena and Nostoc are preferred. Those of the genera Anacystis, Microcystis, Spirulina, Anabaena and Nostoc are especially preferred.

[II] Division Rhodophyta
A. Class PROTOFLORIDEOPHYCEAE
(PROTOFLORIDEAE, BANGIOPHYCEAE)
A-1.
  Order Porphyridiales
A-1-1.
  Family Porphyrdiaceae
  Genus Porphyridium Nägeli (*P. cruentum*), and
  Genus Vanhoeffenia Willie (*V. antractica*).
A-1-2.
  Family Cyanidiaceae
  Genus Cyanidium Geitler (*C. cardarium*).
A-2.
  Order Goniotrichales
A-2-1.
  Family Goniotrichaceae
  Genus Asterocystis Gobi,
  Genus Goniotrichum Kützing (*G. alsidii*).
A-2-2.
  Family Pharagmonemataceae
  Genus Kyliniella Skuja (*K. latrica*), and
  Genus Pharagmonema Zopf (*P. sordidum*).
A-3.
  Order Bangiales
A-3-1.
  Family Erythropeltidaceae
  Genus Erythrocladia Rosenvinge (*E. subintegra*),
  Genus Erythropeltis Schmitz,
  Genus Erythrotrichia Areschoug (*E. carnea*), and
  Genus Porphyropsis Rosenvinge (*P. coccinea*).
A-3-2.
  Family Bangiaceae
  Genus Bangia Lyngbye (*B. fuscopurpurea*), and
  Genus Porphyra Agardh (*P. tenera*).
A-4.
  Order Compsopogonales
A-4-1.
  Family Compsopogonaceae
  Genus Compsopogon Montagne (*C. oishii*).
A-5. Order Rhodochaetales
A-5-1.
  Family Rhodochaetaceae
  Genus Rhodochaete Thuret.

B. Class FLORIDEOPHYCEAE (FLORIDEAE)

B-1. Order Nemaliales
B-1-1. Family Acrochaetiaceae
  Genus Acrochaetium Nägeli,
  Genus Chantransia Fries (*C. secundata*), and
  Genus Rhodochorton Nägeli (*R. howei*).
B-1-2.
  Family Batrachospermaceae
  Genus Batrachospermum Roth (*B. moniliforme*), and
  Genus Sirodotia Kylin (*S. huillense*).
B-1-3.
  Family Lemaneaceae
  Genus Lemanea Bory.
B-1-4.
  Family Naccariaceae
  Genus Naccaria Endlicher.
B-1-5.
  Family Bonnemaisoniaceae
  Genus Asparagopsis Montagne (*A. taxiformis*),
  Genus Bonnemaisonia Agardh (*B. hamifera*),
  Genus Delisea Lamouroux (*D. fimbriata*), and
  Genus Ptilonia J. Agardh (*P. okadai*).
B-1-6.
  Family Thoreaceae
  Genus Thorea Bory (*T. ramosissima*).
B-1-7.
  Family Helminthocladiaceae
  Genus Cumagloea Setchel et Gardner,
  Genus Dermonema (Greville) Harvey (*D. frappieri*),
  Genus Helminthocladia J. Agardh (*H. australis*),
  Genus Liagora Lamouroux (*L. caenomyce*),
  Genus Nemalion Targioni-Tozzetti (*N. vermiculare*), and
  Genus Trichogloes Kützing (*T. requienii*).
B-1-8.

Family Chaetangiaceae
Genus Actinotrichia Decaisne (*A. fragilis*),
Genus Galaxaura Lamouroux (*G. fastigiata*),
Genus Gloiophloea J. Agardh (*G. okamurai*), and
Genus Scinaia Bivona (*S. japonica*).
B-2.
Order Gelidiales
B-2-1.
Family Gelidiaceae
Genus Acanthopeltis Okamura (*A. japonica*),
Genus Gelidiella Feldmann et Hamel (*G. acerosa*),
Genus Gelidium Lamouroux (*G. amansii*),
Genus Pterocladia J. Agardh (*D. tenuis*), and
Genus Yatabelld Okamura (*Y. hirsuta*).
B-3.
Order Cryptonemiales
B-3-1.
Family Cruoriaceae
Genus Cruoria Fries.
B-3-2.
Family Dumontiaceae
Genus Constantinea Postels et Ruprecht (*C. subulifera*).
Genus Dilsea Stackhouse (*D. edulis*),
Genus Dudresnaya Bonnemaison (*D. japonica*),
Genus Dumontia Lamouroux (*D. incrassata*),
Genus Farlowia J. Agardh (*F. irregularis*),
Genus Hyalosiphonia Okamura (*H. caepitosa*),
Genus Neodilsea Tokida (*N. yendoana*), and
Genus Pikea Harvey (*P. californica*).
B-3-3.
Family Rhizophyllidaceae
Genus Chondrococcus Küzing (*C. japonica*),
Genus Contarinia Zanardini (*C. okamurai*), and
Genus Rhodopeltis (Harv.) Schmitz (*R. borealis*).
B-3-4.
Family Squamariaceae
Genus Cruoriopsis Dufour (*C. japonica*),
Genus Hildenbrandia Nardo (*H. rosea, H. rivularis*), and
Genus Peyssonnelia Decaisne (*P. caulifera*).
B-3-5.
Family Corallinaceae
Genus Amphiroa Lamouroux (*A. dilatata*),
Genus Cheilosporum (Aresch.) Yendo (*C. jungermannioides*),
Genus Choreonema Schmitz (*C. thuretii*),
Genus Corallina Lamouroux (*C. officinalis*),
Genus Dermatolithon Foslie (*D. tumidulum*),
Genus Fosliella Howe (*F. zostericola*),
Genus Goniolithon Foslie (*G. sp.*),
Genus Hydrolithon Foslie (*H. reinboldii*),
Genus Jania Lamouroux (*J. arborescens*),
Genus Joculator Manza (*J. maximus*),
Genus Lithophyllum Philippi (*L. yendoi*),
Genus Lithophorella Philippi (*L. sp.*),
Genus Lithothamnion Philippi (*L. simulans*),
Genus Mastophora Harvey (*M. rosea*),
Genus Melobaria Lamouroux, and
Genus Pachyarthron Manza (*P. cretaceum*).
B-3-6.
Family Grateloupiaceae
Genus Aeodes J. Agardh (*A. lanceolata*),
Genus Carpopeltis Schmitz (*C. angusata*),
Genus Cryptonemia J. Agardh (*C. schmitziana*),
Genus Cyrtymenia Schmitz (*C. sparsa*),
Genus Grateloupia Agardh (*G. filicina*),
Genus Halymenia J. Agardh (*H. agardhii*),
Genus Pachymenia J. Agardh (*P. carnosa*),
Genus Polyopes J. Agardh (*P. polyideoides*), and
Genus Prionitis J. Agardh (*P. patens*).
B-3-7.
Family Gloiosiphoniaceae
Genus Gloiostiphonia Ceramichael (*G. capillaris*), and
Genus Schimmelmannia Schousb (*S. plumosa*).
B-3-8.
Family Endocladiaceae
Genus Endocladia J. Agardh, and
Genus Gloeopeltis J. Agardh (*G. tenax*).
B-3-9.
Family Tichocarpaceae
Genus Tichocarpus Ruprecht (*T. crinitus*).
B-3-10.
Family Callimeniaceae
Genus Callophyllis Küzing (*C. crispate*),
Genus Callymenia J. Agardh (*C. perforata*), and
Genus Euthora J. Agardh (*E. fruticulosa*).
B-3-11.
Family choreocolaceae
Genus Choreocolax Reinsch
B-4.
Order Gigartinales
B-4-1.
Family Calosihoniaceae
Genus Bertholdia Schmitz (*B. japonica*), and
Genus Calosiphonia Crouan (*C. vermicularis*).
B-4-2.
Family Nemastomataceae
Genus Nemastoma J. Agardh (*N. nakamurae*),
Genus Platoma (Schousb.) Schmitz (*P. izunosimensis*), and
Genus Schizymenia J. Agardh (*S. dubyi*).
B-4-3.
Family Sebdeniaceae
Genus Sebdenia Berth (*S. Yamadai*).
B-4-4.
Family Gracilariaceae
Genus Ceratodictyon Zanardini (*C. spongiosum*),
Genus Gelidiopsis Schmitz (*G. hachijoensis*),
Genus Gracilaria Greville (*G. verrucosa*), and
Genus Tylotus J. Agardh (*T. lichienoides*).
B-4-5.
Family Plocamiaceae
Genus Plocamium (Lamour.) Lyngbye (*P. telfairiae*).
B-4-6.
Family Sphaerococcaceae
Genus Caulacanthus Kützing (*C. okamurai*),
Genus Phacelocarpus Endlicher et Diesing (*P. japonicus*), and
Genus Sphaerococcus Stackhouse.
B-4-7.
Family Stictosporaceae
Genus Stictosporum Harrey.
B-4-8.
Family Sarcodiaceae
Genus Sarcodia J. Agardh (*S. ceylanica*), and
Genus Trematocarpus Kützing (*T. pygmaeus*).
B-4-9.
Family Furcellariaceae
Genus Furcellaria De Toni, and
Genus Halarachnion Kützing (*H. lattissimum*).
B-4-10.
Family Solieriaceae
Genus Eucheuma J. Agardh (*E. muricatum*),
Genus Meristotheca J. Agardh (*M. papulosa*), Genus Solieria J. Agardh (S. robusta), and
Genus Turnerella Schmitz (T. martensiana).

B-4-11.
Family Rissoellaceae
Genus Rissoella J. Agardh.

B-4-12.
Family Rhabdoniaceae
Genus Catenella Greville (C. opuntia), and
Genus Rhabdonia Harvey.

B-4-13.
Family Rhodophyllidaceae
Genus Rhodophyllis Kützing.

B-4-14.
Family Hypneaceae
Genus Hypnea Kützing (H. charoides).

B-4-15.
Family Mychodeaceae
Genus Mychodea Harvey.

B-4-16.
Family Dicranemataceae
Genus Dicranema Sonder.

B-4-17.
Family Acrotylaceae
Genus Acrotylus J. Agardh.

B-4-18.
Family Phyllophoraceae
Genus Ahnfeltia Fries (A. concinna),
Genus Gymnogongrus Martius (G. flabelliformis),
Genus Phyllophora Greville, and
Genus Stenogramma Harvey (S. interrupta).

B-4-19.
Family Gigartinaceae
Genus Chondrus Stackhouse (C. ocellatum),
Genus Gigartina Stackhouse (G. tenella), and
Genus Iridaea Bory (I. cornucopiae).

B-5.
Order Rhodymeniales

B-5-1.
Family Champiaceae
Genus Champia Desvaux (C. parvula),
Genus Coeloseira Hollenberg (C. pacifica), and
Genus Lomentaira Lyngbye (L. catenata).

B-5-2.
Family Rhodymeniaceae
Genus Botryocladia Kylin (B. leptopoda),
Genus Chrysymenia J. Agardh (C. wrightii),
Genus Coelarthrum Börgesen (C. muelleri),
Genus Cryptarachne Kylin (C. polyglandulosa),
Genus Erythrocolon J. Agardh (E. podagricum),
Genus Fauchea Montagne et Bory (F. spinulosa),
Genus Gloioderma J. Agardh (G. japonica),
Genus Halossaccion Kützing (H. saccatum),
Genus Rhodymenia Greville (R. palmata), and
Genus Weberella Schmitz (W. micans).

B-6.
Order Ceramiales

B-6-1.
Family Ceramiaceae
Genus Acrothamnion J. Agardh (A. pulchellum),
Genus Antithamnion Nägeli (A. nipponicum),
Genus Callithamnion Lyngbye (C. callophyllidicola),
Genus Campylaephora J. Agardh (C. hypnaeoides),
Genus Centroceras Kützing (C. clavulatum),
Genus Ceramium (Roth) Lyngbye (C. kondoi),
Genus Crouania J. Agardh (C. attenuata),
Genus Dasyphila Sonder (D. plumarioides),
Genus Delesseriopsis Okamura (D. elegans),
Genus Euptilota Kützing (E. articulata),
Genus Griffithsia Agardh (G. japonica),
Genus Herpochondria Falkenberg (H. corallinae),
Genus Microcladia Greville (M. elegans),
Genus Monospora Solier (M. tenuis),
Genus Platythamnion J. Agardh (P. yezoense),
Genus Plenosporium Nägeli (P. kobayashii),
Genus Plumaria (Stackh.) Schmitz (P. ramosa),
Genus Plumariella Okamura (P. yoshikawai),
Genus Psilothallia Schmitz (P. dentata),
Genus Ptilota Agardh (P. pectinada),
Genus Reinboldiella De Toni (R. schmitziana),
Genus Rhodocallis Kützing (R. elegans),
Genus Spermothamnion Areschoug (S. endophytica),
Genus Spyridia Harvey (S. filamentosa),
Genus Trailliella Batters (T. intricata), and
Genus Wrangelia Agardh (W. argus).

B-6-2.
Family Delesseriaceae

B-6-2-(1)
Subfamily Delesserioideae
Genus Brachioglossum Kylin (B. ciliatum),
Genus Caloglossa (Harv.) J. Agardh (C. leprieurii),
Genus Delesseria (Lamour.) Kylin (D. violacea),
Genus Hemineura Harvey (H. schmitziana),
Genus Holmesia J. Agardh (H. japonica),
Genus Hyploglossum Kützing (H. geminatum),
Genus Laingia Kylin (L. pacifica), and
Genus Membranoptera Stackhouse (M. robbeniensis), B-6-2-(2)
Subfamily Nitophylloideae
Genus Acrosorium (Zan.) Kylin (A. yendoi),
Genus Erythroglossum (J. Ag.) Kylin (E. repens),
Genus Hypophyllum Kylin (H. midendorfii),
Genus Martensia Hering (M. denticulata),
Genus Myriogramme Kylin (M. polyneura),
Genus Nienburgia Kylin (N. japonica),
Genus Nitophyllum Greville (N. stellatocorticatum),
Genus Phycodrys (Kütz.) Kylin (P. fimbriata),
Genus Polycoryne Skottsberg (P. denticulata), and
Genus Pseudophycodrys Skottsberg (P. rainoskei).

B-6-2(3)
Subfamily Sarcomenioideae
Genus Sarcomenia Sond.
Genus Taenioma J. Agardh (T. perpusillum), and
Genus Vanvoorstia Harvey (V. coccinea).

B-6-3.
Family Rhodomelaceae

B-6-3-(1)
Subfamily Polysiphonioideae
Genus Digenia Agardh (D. simplex),
Genus Polysiphonia Greville (P. morrowii), and
Genus Tolypiocladia Schmitz (T. glomerulata).

B-6-3-(2)
Subfamily Lophothalioideae
Genus Isoptera Okamura (I. regularis),
Genus Lophothalia Kützing, and
Genus Wrightiella Schmitz (W. loochooensis).

B-6-3-(3)
Subfamily Bostrychioideae
Genus Bostrychia Montagne (B. tenella, B. flagellifera, B. tenuis f. simpliciuscula).

B-6-3-(4)
Subfamily Rhodomeloideae
Genus Odonthalia Lyngbye (O. corymbifera), and
Genus Rhodomela Agardh (R. larix).

B-6-3-(5)
Subfamily Chondrioideae
Genus Acanthophora Lamouroux (A. orientalis),

Genus Acrocystis Zanardini (*A. nana*), and
Genus Chondria Agardh (*C. dasyphylla*).

B-6-3-(6)
Subfamily Laurencieae
Genus Laurencia Lamouroux (*L. intermedia*).

B-6-3-(7)
Subfamily Pterosiphonioideae
Genus Pterosiphonia Falkenberg (*P. pennata*), and
Genus Symphiocladia Falkenberg (*S. latiuscula*).

B-6-3-(8)
Subfamily Herposiphonioideae
Genus Herpopteros Falkenberg (*H. zonaricola*), and
Genus Herposiphonia Nägeli (*H. fissidentoides*).

B-6-3-(9)
Subfamily Lophosiphonioideae
Genus Lophosiphonia Falkenberg.

B-6-3-(10)
Subfamily Polyzonioideae
Genus Euzoniella Falkenberg (*E. ocellata*),
Genus Leveillea Decaisne (*L. jungermannioides*), and
Genus Polyzonia Suhr.

B-6-3-(11)
Subfamily Amansioideae
Genus Amansia Lamouroux (*A. japonica*),
Genus Aneura (J. Ag.) W. von Bosse (*A. lorenzii*),
Genus Enantiocladia Falkenberg (*E. okamurai*),
Genus Neurymenia J. Agardh (*N. fraxinifolia*), and
Genus Vidalia Lamouroux (*V. obtusiloba*).

B-6-4.
Family Dasyaceae
Genus Benzaitenia Yendo (*B. yenoshimaensis*),
Genus Dasya Agardh (*D. sessilis*),
Genus Dasyopsis Zanardini (*D. plumosa*), and
Genus Heterostiphonia Montagne (*H. pulchra*).

In the division Rhodophyta, algae belonging to the genera Porphyridium, Porphyra, Helminthocladia, Gelidium, Corallina, Mastophora, Grateloupia, Gloiosiphonia, Gloeopeltis, Nemastoma, Ceratodictyon, Sarcodia, Gymnogongrus, Laingia, and Nitophyllum are preferred. Those of the genera Porphyridium, Porphyra and Gelidium are especially preferred.

[III] Division Chrysophyta

A. Class CHRYSOPHYCEAE

A-1.
Order Chrysomonadales

A-1-1.
Family Chromulinaceae
Genus Amphichrysis Korshikov,
Genus Chromulin Cienkowski, (*C. rosanoffii*),
Genus Chrysapsis Pascher,
Genus Chrysococcus Klebs, and
Genus Kephyrion Pascher.

A-1-2.
Family Mallomonadaceae
Genus Chrysosphaerella Lauterborn (*C. longispina*), and
Genus Mallomonas Perty (*M. caudata*).

A-1-3.
Family Crytophoraceae
Genus Crytophora Pascher,

A-1-4.
Family Isochrysidaceae
Genus Derepyxis Stokes (*D. dispar*), and
Genus Syncrypta Ehrenberg.

A-1-5.
Family Coccolithophoridaceae
Genus Coccolithus Schwarz, and
Genus Hymenomonas Stein.

A-1-6.
Family Synuraceae
Genus Synura Ehrenberg (*S. uvelia*).

A-1-7.
Family Ochromonadaceae)
Genus Chrysobotrys Pascher,
Genus Ochromonas Wystozi, and
Genus Uroglena Ehrenberg (*U. volvox*).

A-1-8.
Family Monadaceae
Genus Monas Müller.

A-1-9.
Family Lepochromonadaceae
Genus Dinobryon Ehrenberg (*D. sertularia*),
Genus Hyalobryon Lauterbon (*H. mucicola*), and
Genus Epipyxis Ehrenberg (*E. tabellariae*).

A-1-10.
Family Prymnesiaceae
Genus Prymnesium Massart.

A-2.
Order Rhizochrysidales

A-2-1.
Family Rhizochrysidaceae
Genus Rhizochrysis Pascher.

A-2-2.
Family Laginiaceae
Genus Chrysopyxis Stein (*C. bipes*), and
Genus Lagynion Pascher (*L. scherffelii*).

A-3.
Order Silicoflagellales (*Silicoflagellata*)

A-3-1.
Family Dictyochaceae
Genus Dictyocha Ehrenberg, and
Genus Mesocena Ehrenberg.

A-4.
Order Chrysocapsales

A-4-1.
Family Chrysocapsaceae
Genus Chrysocapsa Pascher (*C. planctonica*), and
Genus Phaeosphaera W. et G. S. West (*P. perforata*).

A-4-2.
Family Naegeliellaceae
Genus Naegeliella Correns

A-4-3.
Family Hydruraceae
Genus Hydrurus Agardh (*H. foetidus*).

A-5.
Order Chrysosphaerales

A-5-1.
Family Chrysosphaeraceae
Genus Chrysosphaera Pascher, and
Genus Epichrysis Pascher.

A-6.
Order Chrysotrichales

A-6-1.
Family Nematochrysidaceae
Genus Nematochrysis Paschr.

A-6-2.
Family Phaeothamniaceae
Genus Phaeothamnion Lagerheim (*P. confervicola*).

A-6-3.
Family Thallochrysidaceae
Genus Thallochrysis Conrad.

B. Class XANTHOPHYCEAE (HETEROKONTAE)

B-1.

Order Heterochloridales
B-1-1.
Family Heterochloridaceae
Genus Heterochloris Pascher,
Genus Rhizochloris Pascher.
B-2.
Order Heterocapsales
B-2-1.
Family Heterocapsaceae
Genus Botryococcus Kützing (*B. braunii*), and
Genus Gloeochloris Pascher.
B-2-2.
Family Mischococcaceae
Genus Mischococcus Nägeli (*M. confervicola*).
B-3.
Order Heterococcales
B-3-1.
Family Stipitococcaceae
Genus Stipitococcus W. et G. S. West (*S. urceolatus*).
B-3-2.
Family Halosphaeraceae
Genus Botrydiopsis Borzi (*B. arhiza*), and
Genus Halosphaera Schmitz.
B-3-3.
Family Myxochloridaceae
Genus Myxochloris Pascher.
B-3-4.
Family Chlorobotrydaceae
Genus Centritractus Lemmermann (*C. belonophorus*),
Genus Chlorobotrys Bohlin, (*C. regularis*),
Genus Gloeobotrys Pascher, and
Genus Tetraëdriella Pascher.
B-3-5.
Family Chlorotheciaceae
Genus Characiopsis Borzi (*C. minima*),
Genus Chlorothecium Borzi, and
Genus Peroniella Gobi (*P. planctonica*).
B-3-6.
Family Ophiocytiaceae
Genus Ophiocytium Nägeli (*O. majus*).
B-4.
Order Heterotrichales
B-4-1.
Family Toribonemataceae
Genus Bumilleria Borzi, and
Genus Tribonema Derbes et Solier (*T. aequale*).
B-4-2.
Family Heterocloniaceae
Genus Heterodendron Steinecke (*H. viridis*).
B-5.
Order Heterosiphonales
B-5-1.
Family Botrydiaceae
Genus Botrydium Wallroth (*B. granulatum*).
B-5-2.
Family Vaucheriaceae
Genus Vaucheria De Candoile (*V. sessilis*).

C. Class BACILLARIOPHYCEAE (DIATOMS)
C-1.
Order Centrales
C-1-(1)
Suborder Discoidineae
C-1-(1)-1.
Family Discaceae
Genus Arachnodiscus Bailey,
Genus Coscinodiscus Ehrenberg (*C. asteromphalus*),
Genus Cyclotella Kützing,
Genus Planktoniella Shütt (*P. sol*),
Genus Melosira Agardh (*M. varians*),
Genus Skeletonema Greville,
Genus Stephanodiscus Ehrenberg (*S. astaea*),
Genus Stephanopyxis Ehrenberg, and
Genus Thallasiosira Cleve.
C-1-(2)
Suborder Solenoidineae
C-1-(2)-1.
Family Soleniaceae
Genus Rhizosolenia Ehrenberg (*R. eriensis*).
C-1-(3)
Suborder Biddulphioidineae
C-1-(3)-1.
Family Biddulphiaceae
Genus Attheya T. West,
Genus Bacteriostrum Shadbolt,
Genus Biddulphia Gray (*B. pulchella*),
Genus Chaetocerus Ehrenberg (*C. densus*), and
Genus Triceratum Ehrenberg.
C-1-(4)
Suborder Rutilarioineae
C-1-(4)-1.
Family Rutilariaceae
Genus Rutilaria Greville (*R. edentata*).
C-2.
Order Pennales
C-2-(1)
Suborder Araphidineae
C-2-(1)-1.
Family Fragilariaceae
Genus Asterionella Hassall (*A. formosa*),
Genus Ceratoneis Ehrenberg,
Genus Diatoma De Candolle,
Genus Fragilaria Lyngbye (*F. capucina*),
Genus Rhabdonema Kützing,
Genus Synedra Ehrenberg (*S. gracilis*), and
Genus Tabellaria Ehrenberg (*T. fenestrata*).
C-2-(2)
Suborder Raphidineae
C-2-(2)-1.
Family Eunotiaceae
Genus Eunotia Ehrenberg (*E. chasei*).
C-2-(3)
Suborder Monoraphidineae
C-2-(3)-1.
Family Achnantheaceae
Genus Achnanthes Bory (*A. inflata*), and
Genus Cocconeis Ehrenberg (*C. placentula*).
C-2-(4)
Suborder Biraphidineae
C-2-(4)-1.
Family Naviculaceae
Genus Amphipleura Kützing (*A. pellucid*),
Genus Amphiprora Ehrenberg (*A. alata*),
Genus Amphora Ehrenberg (*A. ovalis*),
Genus Cymbella Agardh (*C. tumida*),
Genus Frustulia Rabenhorst (*F. rhomboides*),
Genus Gomphonema Agardh (*G. acuminatum*),
Genus Navicuta Bory (*N. radiosa*),
Genus Pinnularia Ehrenberg (*P. viridis*),
Genus Pleurosigma W. Smith, and
Genus Stauroneis Ehrenberg.
C-2-(4)-2.
Family Epithemiaceae
Genus Epithemia Brebisson (*E. turgida*), and
Genus Rhopalodia O. Müeller (*R. gibba*).
C-2-(4)-3.

Family Nitzschiaceae
Genus Bacillaria Gmelin, and
Genus Nitzschia Hassall (*N. vitrea*).
C-2-(4)-4.
Family Surirellaceae
Genus Campylodiscus Ehrenberg,
Genus Cymatopleura W. Smith, and
Genus Surirella Turpin (*S. biserrata*).

In the division Chrysophyta, algae belonging to the genera Chromulin, Botryococcus, Mischococcus, Coscinodiscus, Skeletonema, Chaetocerus, Fragilaria, and Navicula are prepared. Those of the genera Coscinodiscus, Sleletonema, Chaetocerus, and Navicula, are especially preferred.

[IV] Division Pyrrhophyta

A. Class CRYPTOPHYCEAE

A-1.
Order Cryptomonadales
A-1-1.
Family Cryptomonadaceae
Genus Chroomonas Hansgirg,
Genus Cryptochrisis Pascher,
Genus Cryptomonas Ehrenberg (*C. erosa*),
Genus Cyatomonas Formentel, and
Genus Rhodomonas Karsten.
A-1-2.
Family Nephroselmidaceae
Genus Nephroselmis Stein, and
Genus Protochrysis Pascher.
A-2.
Order Cryptocapsales
A-2-1.
Family Phaeococcaceae
Genus Phaeococcus Borzi.
A-3.
Order Cryptococcales
A-3-1.
Family Cryptococcaceae
Genus Tetragonidium Pascher.

B. Class DINOPHYCEAE

B-(A)
Subclass DESMOPHYCIDAE
B-(A)-1.
Order Desmomonadales
B-(A)-1-1.
Family Desmocarpaceae
Genus Desmocarpa Crouan, and
Genus Desmomastix Pascher.
B-(A)-2.
Order Thecatales
B-(A)-2-1.
Family Prorocentraceae
Genus Exuviaella Cienkowski, and
Genus Prorocentrum Ehrenberg.
B-(A)-3.
Order Dinophysiales
B-(A)-3-1.
Family Dinophysiaceae
Genus Dinophysis Ehrenberg, and
Genus Pharacroma Stein.
B-(A)-3-2.
Family Amphisoleniaceae
Genus Amphisolenia Stein.
B-(B)
Subclass DINOPHYCIDAE
B-(B)-1.
Order Peridiniales
B-(B)-1-1.
Family Pronoctilucaceae
Genus Pronoctiluca Fabre-Domerque.
B-(B)-1-2.
Family Gymnodiniaceae
Genus Amphidinium Claparede et Lackmann, and
Genus Gymnodinium Stein (*G. neglectum*).
B-(B)-1-3.
Family Polykrikaceae
Genus Polykrikos Bütschli.
B-(B)-1-4.
Family Noctilucaceae
Genus Noctiluca Suriray (*N. scintillans*).
B-(B)-1-5.
Family Warnowiaceae
Genus Erythropsis Hertwig, and
Genus Warnowia Lindemann.
B-(B)-1-6.
Family Blastodiniaceae
Genus Blastodinium Chatton, and
Genus Oodinium Ohatton.
B-(B)-1-7.
Family Glenodiniaceae
Genus Glenodinium Stein (*G. cinctum*).
B-(B)-1-8.
Family Protoceratiaceae
Genus Protoceratium Bergh.
B-(B)-1-9.
Family Gonyaulaxaceae
Genus Gonyaulax Diesing.
B-(B)-1-10.
Family Peridiniaceae
Genus Peridinium Ehrenberg (*P. wisconsinensis*).
B-(B)-1-11.
Family Ceratiaceae
Genus Ceratium Schrank (*C. hirundinella*).
B-(B)-1-12.
Family Goniodomaceae
Genus Goniodoma Stein.
B-(B)-1-13.
Family Ceratocoryaceae
Genus Ceratocorys Stein.
B-(B)-1-14.
Family Podolampaceae
Genus Podolampas Stein.
B-(B)-2.
Order Dinocapsales
B-(B)-2-1.
Family Dinocapsaceae
Genus Glenodinium Klebs (*G. montanum*), and
Genus Urococcus Kützing (*U. insignis*).
B-(B)-3.
Order Rhizodinales
B-(B)-3-1.
Family Rhizodiniaceae
Genus Dinamoebidium Pascher.
B-(B)-4.
Order Dinococcales
B-(B)-4-1.
Family Dinococcaceae
Genus Cystodinium Klebs (*C. iners*).
Genus Hypnodinium Klebs,
Genus Stylodinium Klebs, and
Genus Tetradinium Klebs (*T. javanicum*).
B-(B)-5.
Order Dinotrichales B-(B)-5-1.
Family Dinotrichaceae
Genus Dinothrix Pascher (*D. paradoxa*).
B-(B)-5-2.
Family Dinocloniaceae
Genus Dinoclonium Pascher (*D. conradi*).

C. Class CHLOROMONADOPHYCEAE

C-1.
Order Chloromonadales
C-1-1.
Family Chloromonadaceae
Genus Gonyostmum Diesing (*G. semen*),
Genus Merotrichia Mereschkowski (*M. ca itata*),
Genus Trentonia Stokes, and
Genus Vacuolaria Cienkowski.

In the division Pyrrhophyta, algae belonging to the genera Exuviaella and Amphidinium are preferred.

[V] Division Phaeophyta

A. Class ISOGENERATAE

A-1.
Order Ectocarpales
A-1-1.
Family Ectocarpaceae
Genus Bodanella W. Zimmermann (*B. lauterbornii*),
Genus Ectocarpus Lyngbye (*E. breviarticulatus*),
Genus Feldmannia Hamel,
Genus Pleurocladia Gran,
Genus Pylaiella Bory (*P. littoralis*), and
Genus Sorocarpus Pringscheim (*S. uvaeformis*).
A-1-2.
Family Ralfsiaceae
Genus Heribaudiella Gomont (*H. fluviatilis*),
Genus Lithoderma Areschoug, and
Genus Ralfsia Berk (*R. fugiformis*).
A-2.
Order Sphacelariales
A-2-1.
Family Sphacelariaceae
Genus Chaetopteris Kützing,
Genus Sphacelaria Lyngbye (*S. furcigera*), and
Genus Sphacella Reinke.
A-2-2.
Family Stypocaulaceae
Genus Halopteris Kützing (*H. filicina*), and
Genus Stypocaulon Kützing.
A-2-3.
Family Cladostephaceae
Genus Cladostephus J. Agardh.
A-2-4.
Family Choristocarpaceae
Genus Choristocarpus Zanardini.
A-3.
Order Cutleriales
A-3-1.
Family Cutleriaceae
Genus Cutleria Greville (*C. cylindrica*), and
Genus Zanardina Nardo.
A-4.
Order Tilopteridales
A-4-1.
Family Tilopteridaceae
Genus Haplospora Kjellman, and
Genus Tilopteris Kützing.
A-5.
Order Dictyotales A-5-1.
Family Dictyotaceae
Genus Dictyopteris Lamouroux (*D. latiuscula*),
Genus Dictyota Lamouroux (*D. dichotoma*),
Genus Dilophus J. Agardh (*D. okamurai*),
Genus Distromium Levring (*D. repens*),
Genus Homoestrichus J. Agardh (*H. flabellatus*),
Genus Pachydictyon J. Agardh (*P. coriaceum*),
Genus Padina Adanson (*P. arborescens*),
Genus Pocockiella Papenfuse (*P. variegata*),
Genus Spathoglossum Kützing (*S. pacificum*),
Genus Stypopodium Kützing (*S. zonale*), and
Genus Zonaria J. Agardh (*Z. diesingiana*).

B. Class HETEROGENERATAE

B-1.
Order Chordariales
B-1-1.
Family Myrionemataceae
Genus Compsonema Kuckuck, and
Genus Myrionema Greville.
B-1-2.
Family Elachistaceae
Genus Elachista Duby (*E. tainiaeformis*), and
Genus Halothrix Reinke (*H. ambigua*).
B-1-3.
Family Leathesiaceae (Corynophloeaceae)
Genus Corynophloea Kützing,
Genus Leathesia S. F. Gray (*L. difformis*), and
Genus Pterospongium Nägeli (*P. rugosum*).
B-1-4.
Family Chordariaceae (Mesogloiaceae)
Genus Chordaria Agardh (*C. flagelliformis*),
Genus Cladosiphon Kützing (*C. okamuranus*),
Genus Eudesme J. Agardh (*E. riescens*),
Genus Heterochordaria Setchell et Gardner (*H. abietina*),
Genus Mesogloia Agardh,
Genus Papenfussiella Kylin (*P. kuromo*),
Genus Saundersella Kylin (*S. simplex*),
Genus Sphaerotrichia Kylin (*S. divaricata*), and
Genus Tinocladia Kylin (*T. crassa*).
B-1-5.
Family Spermatochnaceae
Genus Ishige Yendo (*I. okamurai*),
Genus Myelophycus Kjellman (*M. simplex*), and
Genus Nemacystus Derbes et Solier (*N. decipiens*).
B-1-6.
Family Acrothricaceae
Genus Acrothrix Kylin (*A. pacifica*).
B-1-7.
Family Chordariopsidaceae
Genus Chordariopsis Kylin.
B-1-8.
Family Splachnidiaceae
Genus Splachnidium Greville.
B-2.
Order Sporochnales
B-2-1.
Family Sporochnaceae
Genus Carpomitra Kützing (*C. cabrerae*),
Genus Nereia Zanardini (*N. intricata*), and
Genus Sporochnus Agardh (*S. scoparius*).
B-3.
Order Desmarestiales
B-3-1.
Family Arthrocladiaceae
Genus Arthrocladia Duby.

B-3-2.
Family Desmarestiaceae
Genus Desmarestia Lamouroux (*D. ligutat*).
B-4.
Order Dictyosiphonales
B-4-1.
Family Striariaceae
Genus Kjellmania Reinke (*K. arasakii*),
Genus Stictyosiphon Kützing, and
Genus Striaria Greville (*S. attenuata*).
B-4-2.
Family Giraudiaceae
Genus Giraudia Derbes et Solier.
B-4-3.
Family Myriotrichiaceae
Genus Myriotrichia Harvey.
B-4-4.
Family Punctariaceae (Asperococcaceae)
Genus Asperococcus Lamouroux (*A. bullosus*),
Genus Colpomenia Derbes et Solier (*C. sinuosa*),
Genus Endarachne J. Agardh (*E. binghamiae*),
Genus Hydroclathrus Bory (*H. clathratus*),
Genus Melanosiphon Wynne (*M. intestinales*),
Genus Petalonia Derbes et Solier (*P. fasia*),
Genus Punctaria Greville (*P. latifolia*),
Genus Scytosiphon Agardh (*S. lomentaria*), and
Genus Soranthera Postels et Ruprecht (*S. ulvoidea*).
B-4-5.
Family Chnoosporaceae
Genus Akkesiphycus Yamada et Tanaka (*A. lubricum*), and
Genus Chnoospora J. Agardh (*C. implexa*).
B-4-6.
Family Dictyosiphonaceae
Genus Coilodesme Stroemfelt (*C. japonica*), and
Genus Dictyosiphon Greville (*D. foeniculaceus*).
B-5.
Order Laminariales
B-5-1.
Family Chordaceae
Genus Chorda Stackhouse (*C. filum*).
B-5-2.
Family Laminariaceae
Genus Agarum Bory (*A. criburosum*),
Genus Arthrothamnus Ruprecht (*A. bifidus*),
Genus Costaria Greville (*C. costata*),
Genus Cymathere J. Agardh (*C. triplicata*),
Genus Hedophyllum Setchell (*H. Kuroshioense*),
Genus Kjellmaniella Miyabe (*K. gyrata*),
Genus Laminaria Lamouroux (*L. japonica*),
Genus Streptophyllum Kiyabe et Nagai (*S. spirae*), and
Genus Thallassiophyllum Postels et Ruprecht (*T. clathrus*).
B-5-3.
Family Lessoniaceae
Genus Lessonia Bory,
Genus Macrocystis Agardh (*M. pyrifera*), and
Genus Nereocystis Postels et Ruprecht.
B-5-4.
Family Alariaceae
Genus Alaria Greville (*A. crassifolia*),
Genus Ecklonia Hornemann (*E. cava*),
Genus Eckloniopsis Okamura (*E. radicosa*),
Genus Eisenia Areschoug (*E. bicyclis*),
Genus Pleuropterum Miyabe et Nagai (*P. paradiseum*), and
Genus Undaria Suringar (*U. pinnatifida*).

C. Class CYCLOSPOREAE
C-1.
Order Fucales
C-1-1.
Family Ascoseiraceae
Genus Ascoseira Skottsberg.
C-1-2.
Family Durvilleaceae
Genus Durvillea Bory.
C-1-3.
Family Notheiaceae (Hormosiraceae)
Genus Hormosira (Endl.) Meneghini, and
Genus Notheia Harvey.
C-1-4.
Family Fucaceae
Genus Fucus L. (*F. evanscens*),
Genus Pelvetia Decne (*P. wrightii*),
Genus Phyllospora Agardh, and
Genus Scytothalia Greville.
C-1-5.
Family Himanthaliaceae
Genus Himanthalia Lyngbye.
C-1-6.
Family Cystoseiraceae
Genus Cystophyllum J. Agardh (*C. sisymbrioides*),
Genus Cystoseira Agardh (*C. prolifera*), and
Genus Halidrys Lyngbye.
C-1-7.
Family Sargassaceae
Genus Acystis Schiffner,
Genus Coccophora Greville (*C. langsdorfii*),
Genus Hizikia Okamura (*H. fusiforme*),
Genus Sargassum Agardh (*S. fulvellum*), and
Genus Turvinaria Lamouroux (*T. ornata*).

In the division Phaeophyta, algae belonging to the genera Sphacelaria, Papenfussiella, Nemacystus, Colpomenia, Kjellmaniella, Laminaria, Macrocystis, Eisenia, and Undaria are preferred. Those of the genera Nemacystus, Laminaria and Undaria are especially preferred.

[VI] Division Euglenophyta

A. Class EUGLENOPHYCEAE

A-1.
Order Euglenales
A-1-1.
Family Euglenaceae
Genus Ascoglena Stein,
Genus Cryptoglena Ehrenberg,
Genus Euglena Ehrenberg (*E. gracilis*),
Genus Eutreptia Perty (*E. viridis*),
Genus Lepocinclis Perty (*L. fusiformis*),
Genus Phacus Dujardin (*P. acuminatus*), and
Genus Trachelomonas Ehrenberg [including Strobomonas Deflandre] (*T. volvocina*).
A-1-2.
Family Astasiaceae
Genus Astasia Ehrenberg (*A. lagenula*), and
Genus Distigma Ehrenberg (*D. proteus*).
A-1-3.
Family Rhynchopodaceae
Genus Rhynchopus Skuja.
A-1-4.
Family Peranemaceae
Genus Anisonema Dujardin (*A. acinus*),
Genus Entosiphon Stein (*E. sulcatum*),
Genus Euglenopsis Klebs, Genus Peranema Dujardin (*P. trichophorum*),
Genus Petalomonas Stein, and
Genus Uroceolus Mereschkowsky.
A-1-5.
Family Rhizaspidaceae
Genus Rhizaspis Skuja.
A-2.
Order Colaciales
A-2-1.
Family Colaciaceae
Genus Colacium Ehrenberg (*C. arbuscula*).

In the division Euglenophyta, algae of the genus Euglena are preferred.

[VII] Division Chlorophyta

A. Class CHLOROPHYCEAE

A-1.
Order Volvocales
A-1-1.
Family Chlamydomonadaceae
Genus Carteria Diesing (*C. miwae*),
Genus Chlamydomonas Ehrenberg (*C. nivalis*),
Genus Eudorina Ehrenberg (*E. unicocca*),
Genus Gonium Müller (*G. pectorale*),
Genus Pandorina Bory (*P. morum*),
Genus Pascheriella Korshikov,
Genus Platidorina Kofoid (*P. caudata*),
Genus Platymonas G.S. West,
Genus Pleodorina Shaw (*P. californica*),
Genus Polytoma Ehrenberg, and
Genus Volvox (L.) Ehrenberg (*V. aureus*).
A-1-2.
Family Haematococcaceae
Genus Haematococcus Agardh (*H. lacustris*).
A-1-3.
Family Polyblepharidaceae
Genus Polyblepharides Dangeard, and
Genus Pyraminonas Schmarda.
A-1-4.
Family Phacotaceae
Genus Coccomonas Stein,
Genus Dysmorphococcus Takeda,
Genus Phacotus Perty (*P. lenticularis*), and
Genus Pleromonas Seligo (*P. aculeata*).
A-2.
Order Tetrasporales
A-2-1.
Family Tetrasporaceae
Genus Apiocystis Nägeli (*A. brauniana*),
Genus Collinsiella Setchell et Gardner (*C. tuberculata*),
Genus Schizochlamys A. Braun, and
Genus Tetraspora Link (*E. lubrica*).
A-2-2.
Family Palmellaceae
Genus Askenasyella Schmidle (*A. chlamydopus*),
Genus Asterococcus Scherffel (*A. superbus*),
Genus Coccomyxa Schmidle,
Genus Elakatothrix Wille (*E. gelatinosa*),
Genus Gloeocystis Nägeli (*G. ampla*),
Genus Palmella Lyngbye (*P. miniata*),
Genus Palmodictyon Kützing (*P. viride*), and
Genus Sphaerocystis Chodat (*S. schroeteri*).
A-2-3.
Family Chlorangiaceae
Genus Chlorangium Stein,
Genus Hormotila Borzi,
Genus Prasinocladus Kuckuck (*P. lubricus*), and
Genus Stylosphaeridium Geitler.
A-3.
Order Chlorococcales
A-3-1.
Family Chlorococcaceae
Genus Characium A. Braun (*C. ambiguum*),
Genus Chlorochytrium Cohn,
Genus Chlorococcum Fries (*C. echinozygotum*),
Genus Kentrosphaera Borzi,
Genus Rhodochytrium Lagerheim,
Genus Schroederia Lemmermann (*S. setigera*), and
Genus Trebouxia De Puymaly (symbiotic algae on lichens).
A-3-2.
Family Eremosphaeraceae
Genus Eremosphaera De Bary.
A-3-3.
Family Chlorellaceae
Genus Acanthosphaera Lemmermann,
Genus Chlorella Beijerinck (*C. vulgaris*),
Genus Golenkinia Chodat (*G. radiata*),
Genus Micractinium Fresenius (*M. pusillum*),
Genus Polyedriopsis Schmidle (*P. spinulosa*),
Genus Radiococcus Schmidle,
Genus Tetraëdron Kützing (*T. regulare*), and
Genus Trochiscia Kutzing (*T. aspera*).
A-3-4.
Family Oocystaceae
Genus Bohlinia Lemmermann,
Genus Chodatella Lemmerman,
Genus Desmatractum W. et G.S. West (*D. bipyramidatum*),
Genus Franceia Lemmermann (*F. tuberculata*),
Genus Gloeotaenium Hansgirg,
Genus Lagerheimia Chodat,
Genus Makinoella Okada (*M. tosaensis*),
Genus Nephrocytium Nägeli (*N. lunatus*),
Genus Oocystis Nägeli (*O. borgei*), and
Genus Scotiella Fritsch (*S. nivalis*).
A-3-5.
Family Selenastraceae
Genus Actinastrum Lagerheim (*A. hantzii*),
Genus Ankistrodesmus Corda (*A. falcatus*),
Genus Closteriopsis Lemmermann (*C. longissima*),
Genus Dactylococcus Nägeli,
Genus Kirchneriella Schmidle (*K. lunaris*),
Genus Quadrigula Printz (*Q. chodatii*), and
Genus Selenastrum Reinsch (*S. gracile*).
A-3-6.
Family Dictyosphaeraceae
Genus Dictyosphaerium Nägeli (*D. ehrenbergianum*),
Genus Dimorphococcus A. Braun (*D. lunatus*), and
Genus Westella De Wildemann.
A-3-7.
Family Hydrodictiaceae
Genus Euastropsis Lagerheim (*E. richteri*),
Genus Hydrodictyon Roth (*H. reticulatum*),
Genus Pediastrum Meyen (*P. simplex*), and
Genus Sorastrum Kützing (*S. spinulosum*).
A-3-8.
Family Coelastraceae
Genus Coelastrum Nägeli (*C. reliculatum*),
Genus Crucigenia Morren (*C. tetrapedia*),
Genus Pseudotetradesmus Hirose et Akiyama,
Genus Scenedesmus Meyen (*S. quadricauda*),
Genus Tetradesmus G. M. Smith (*T. wisconsinensis*), and Genus Tetrastrum Ohodat (*T. elegans*).
A-3-9.
  Family Protosiphonaceae
  Genus Protosiphon Klebs (*P. botryoides*).
A-4.
  Order Ulotrichales
A-4-(1)
  Suborder Ulotrichineae
A-4-(1)-1.
  Family Ulotrichaceae
  Genus Binuclearia Wittrock (*B. tectorum*),
  Genus Geminella Turpin (*G. mutabilis*),
  Genus Hormidium Kützing (*H. klebsii*),
  Genus Radiophilum Schmidle (*R. conjunctirum*),
  Genus Rhaphidonema Lagerheim (*R. nivale*),
  Genus Stichococcus Nägeli (*S. bacilaris*),
  Genus Ulothrix Kützing (*U. flacca, U. Zonata*), and
  Genus Uronema Lagerheim.
A-4-(1)-2.
  Family Microsporaceae
  Genus Microspora Thuret (*M. willeana*).
A-4-(1)-3.
  Family Schizomeridaceae
  Genus Schizomeris Kützing (*S. leibleinii*).
A-4-(1)-4.
  Family Cylindrocapsaceae
  Genus Cylindrocapsa Reinsch (*C. geminella*).
A 4-(2)
  Suborder Ulvineae
A-4-(2)-1.
  Family Ulvaceae
  Genus Enteromorpha Link (*E. prolifera, E. intestinalis*),
  Genus Letterstedtia Areschoug (*L. japonica*),
  Genus Monostroma Thuret (*M. nitidum*), and
  Genus Ulva L. (*U. pertusa*).
A-4-(3)
  Suborder Prasiolineae
A-4-(3)-1.
  Family Prasiolaceae
  Genus Prasiola (Ag.) Meneghini (*P. japonica*), and
  Genus Schizogonium Kützing (*S. murale*).
A-4-(4)
  Suborder Sphaeropleineae
A-4-(4)-1.
  Family Sphaeropleaceae
  Genus Sphaeroplea Agardh (*S. annulina*).
A-5.
  Order Cladophorales
A-5-1.
  Family Cladophoraceae
  Genus Basicladia Hoffmann et Tilden,
  Genus Chaetomorpha Kützing (*C. okamurai, C. cvassa*),
  Genus Cladogonium Hirose et Akiyama (parasitic algae),
  Genus Cladophora Kützing (*C. glomerata, C. (Aegaglopila) sauteri C. wrightiana*),
  Genus Microdictyon Decne (*M. japonicum*),
  Genus Pithophora Wittrock (*P. zelleri*),
  Genus Rhizoclonium Kützing (*R. tortuosum*),
  Genus Spongomorpha Kützing (*S. heterocladia*),
  Genus Urospora Areschoug (*U. penicilliformis*), and
  Genus Willeella Börgesen (*W. japonica*).
A-6.
  Order Chaetophorales
A-6-1.
  Family Chaetophoraceae
  Genus Aphanochaeta A. Braun (*A. repens*),
  Genus Chaetonema Nawakowski (*C. irregulare*),
  Genus Chaetopeltis Berthold,
  Genus Chaetophora Schrank (*C. elegans*),
  Genus Cloniphora Tiffany (*C. plumosa*),
  Genus Draparnaldia Bory (*D. glomerata*),
  Genus Draparnaldiopsis Smith et Klyver (*D. alpina*),
  Genus Endoderma Lagerheim,
  Genus Fritschiella Lyengar (*F. tuberosa*),
  Genus Microthamnion Nägeli (*M. kuetzingianum*),
  Genus Protoderma Kützing,
  Genus Pseudoulvella Wille,
  Genus Saprochaete Coner et Shanor (saprophytic algae),
  Genus Stigeoclonium Kützing (*S. lubricum*), and
  Genus Thamniochaete Gay (*T. huberi*).
A-6-2.
  Family Trentepohliaceae
  Genus Cephaleuros Kunze (*C. virescens*),
  Genus Chlorotylium Kützing,
  Genus Ctenocladus Borzi,
  Genus Fridaea Schmidle,
  Genus Gomontia Bornet et Flahault,
  Genus Gongrosira Kützing (*G. debaryana*),
  Genus Leptosira Borzi (*L. terricola*),
  Genus Phycopeltis Millardet (*P. irregularis*),
  Genus Physolium Printz (*P. monilia*), and
  Genus Trentepohlia Martens (*T. aurea*).
A-6-3.
  Family Coleochaetaceae
  Genus Coleochaete Brebisson (*C. pulvinata*).
A-6-4.
  Family Chaetosphaeridiaceae
  Genus Chaetosphaeridium Klebahn (*C. globosum*),
  Genus Conochaete Klebahn (*C. comosa*),
  Genus Dicranochaete Hieronymus (*D. reniformis*), and
  Genus Oligochaetophora G. S. West (*O. simplex*).
A-6-5.
  Family Protococcaceae
  Genus Protococcus Agardh [Pleurococcus Meneghini] (*p. viridis* adhering to stone hedges or tree trunks).
A-7.
  Order Oedogoniales
A-7-1.
  Family Oedogoniaceae
  Genus Bulbochaete Agardh (*B. brebissonii*),
  Genus Oedocladium Stahl (*O. operculatum*), and
  Genus Oedogonium Link (*O. varians*).
A-8.
  Order Zygnematales
A-8-1.
  Family Mesotaeniaceae
  Genus Cylindrocystis Meneghini (*C. crassa*),
  Genus Mesotaenium Nägeli (*M. greyii*),
  Genus Netrium Nägeli (*N. digitus*),
  Genus Roya W. et G. S. West (*R. obtusa*), etc.
  Genus Spirotaenia Brebisson (*S. condensata*).
A-8-2.
  Family Gonatozygaceae
  Genus Genicularia De Bary, and pl Genus Gonatozygon De Bary (*G. aculeatum*).
A-8-3.
  Family Zygnemataceae
  Genus Debarya Wittrock,
  Genus Mougeotia Agardh (*M. scalaris*),
  Genus Mougeotiopsis Palla, Genus Mougeotiella Yamagishi (*M. drouetii*),
Genus Neozygnema Yamagishi (*N. laevisporum*),
Genus Sirocladium Randhawa,
Genus Sirogonium Kützing (*S. sticticum*),
Genus Spirogyra Link (*S. crassa*),
Genus Temnogametum W. et G. S. West (*T. boreale*),
Genus Temnogyra Lewis (*T. collinsii*),
Genus Zygnema Agardh (*Z. cruciatum*),
Genus Zygnemopsis Transeau (*Z. quadrata*), and
Genus Zygogonium Kützing (*Z. ericetorum*).

A-8-4.
Family Desmidiaceae
Genus Arthrodesmus Ehrenberg (*A. triangularis*),
Genus Closterium Nitzsch (*C. moniliforme*),
Genus Cosmarium Corda (*C. cymatopleurum*),
Genus Cosmocladium Brebisson (*C. constrictum*),
Genus Desmidium Agardh (*D. aptogonum*),
Genus Docidium Brebisson (*D. undulatum*),
Genus Euastrum Ehrenberg (*E. oblongum*),
Genus Gymnozyga Ehrenberg (*G. moniliformis*),
Genus Hyalotheca Ehrenberg (*H. dissiliens*),
Genus Micrasterias Agardh (*M. radiata*),
Genus Onychonema Wallich (*O. leave*),
Genus Oöcardium Nägeli (*O. stratum*),
Genus Penium Brebisson (*P. margaritaceum*),
Genus Pleurotaenium Nägeli (*P. ehrenbergii*),
Genus Sphaerozosma Corda (*S. aubertianum*),
Genus Spnondylosium Brebisson (*S. planum*),
Genus Staurastrum Meyen (*S. punctulatum*),
Genus Tetmemorus Ralfs (*T. laevis*), and Genus Xanthidium Ehrenberg (*X. antilopaeum*).

A-9.
Order Siphonales
A-0-1.
Family Caulerpaceae
Genus Bryopsis Lamouroux (*B. plumosa*),
Genus Caulerpa Lamouroux (*C. okamurai*),
Genus Pseudobryopsis Berthold (*P. hainanensis*).

A-9-2.
Family Derbesiaceae
Genus Derbesia Solier (*D. lamourouxii*).

A-9-3.
Family Dasycladaceae
Genus Acetabularia Lamouroux (*A. ryukyuensis*),
Genus Bornetella Munier-Chalmer (*B. ovalis*),
Genus Cymopolia Lamouroux (*C. vanbossei*),
Genus Dasycladus Agardh,
Genus Halicoryne Harvery (*H. wrighti*), and
Genus Neomeris Lamouroux (*N. annulata*).

A-9-4.
Family Codiaceae
Genus Avrainvilla Börgesen (*A. ryukyuensis*),
Genus Chlorodesmis Bailey et Harvey (*C. comosa*),
Genus Codium Stackhouse (*C. fragile*),
Genus Halimeda Lamouroux (*H. opuntia*),
Genus Tydemania W. van Bosse (*T. expeditionis*), and
Genus Udotea Lamouroux (*U. javensis*).

A-9-5.
Family Valoniaceae
Genus Anacyomena Lamouroux (*A. wrightii*),
Genus Boodlea Murray et De Toni (*B. coacta*),
Genus Ohamaedoris Montagne (*C. orientalis*),
Genus Cladophoropsis Börgesen (*C. zollingeri*),
Genus Dictyosphaeria Decaisne (*D. cavernosa*),
Genus Siphonocladus Schmitz (*S. tropicus*),
Genus Struvea Sonder (*S. delicatula*), and
Genus Valonia Ginnani (*V. utricularis*).

A-9-6.
Family Chaetosiphonaceae
Genus Chaetosiphon Huber.

A-9-7.
Family Phillosiphonaceae
Genus Phyllosiphon Kühn (*P. arisari*).

A-9-8.
Family Dichotomosiphonaceae
Genus Dichotomosiphon Ernst (*D. tuberosus*), and
Genus Pseudodichotomosiphon Yamada (*P. constricta*).

In the division Chlorophyta, algae belonging to the genera Chlamydomonas, Chlorella, Scenedesmus, Protosiphon, Ulothrix, Microspora, Enteromorpha, Prasiola, Cladophora, Spongomorpha, Chaetophora, Trentepohlia, Protococcus, Spirogyra, Desmidium, Bryopsis, and Acetabularia are preferred. Those of the genera Chlamydomonas, Chlorella, Scenedesmus, and Cladophora are especially preferred.

[VIII] Division Charophyta

A. Class CHAROPHYCEAE

A-1.
Order Sycidiales

A-2.
Order Trochiliscales

A-3.
Order Charales

A-3-1.
Family Characeae
Genus Chara I. (*C. braunii, C. globularis*),
Genus Lamprothamnium Groves (*L. papillosum*),
Genus Lychnothamnus (Rupr.) Leonhardi,
Genus Nitella Agardh (*N. flexilis*),
Genus Nittellopsis Hy (*N. obtusa*), and
Genus Tolypella Leonhardi (*T. gracilis*).

A-3-2.
Family Paleocharaceae

A-3-3.
Family Clavatoraceae

A-3-4.
Family Lagynophoraceae

In the division Charophyta, algae belonging to the genus Lamprothamnium are preferred.

Especially preferred algae to which the method of this invention is applicable include those of the genera Anacystis, Microcystis, Spirulina, Anabaena and Nostoc (Division Cyanophyta); those of the genera Porphydridium, Porphyra and Gelidium (Division Rhodophyta); those of the genera Coscinodiscus, Skeletonema, Chaetocerus, and Navicula (Division Chrysophyta); those of the genera Exuviaella, Amphidinium, and Gymnodinium (Division Pyrrhophyta); those of the genera Nemacystus, Laminaria and Undaria (Division Phaeophyta); and those of the genera Chlamydomonus Chlorella, Scenedesmus and Cladophora (Division Chlorophyta).

The cultivation of the algae in accordance with the method of this invention is carried out in a light field which is substantially free from light of wavelengths of not more than 340 nm, preferably not more than 360 nm, more preferably not more than 380 nm.

The term "optical field substantially free from light of wavelengths of not more than x nm", means that preferably it is a light field completely free from light of wavelengths of not more than x nm, but it does not preclude the presence of small amounts of light of wavelengths of not more than x nm which do not adversely affect the cultivation of algae in accordance with this invention. Hence, in cultivation under sunlight, the light field is desirably be the one which inhibits the transmission of the light of wavelengths of not more than x nm by at least 70%, preferably at least 80%, more preferably 90 to 100%. In cultivation under artificial light, the cultivation is desirably carried out under the irradiation of artificial light in which the amount of light of the aforesaid wavelength region is not more than 500 $\mu W/cm^3$, preferably not more than 250 $\mu W/cm^3$, more preferably 50 to 0 $\mu W/cm^3$.

Growth of algae by photosynthesis requires the irradiation of certain amounts of light in the visible region, and generally, it is desirable to perform cultivation in a light field in which light of wavelengths of at least 550 nm, preferably at least 450 nm, can be present. The intensity of light of wavelengths of at least 550 nm varies greatly according to the type of the algae, the depth of water, etc., and cannot be definitely determined. However, suitable quantities and intensities of light would be able to be determined easily by any one skilled in the art by performing small-scale experiments.

Light of wavelengths of 340 nm to 550 nm, i.e. near ultraviolet to green light, may or may not be present in the light field. There is a general tendency that the amount of violet to green light having a wavelength region of 400 to 550 nm is preferably minimized for the growth of algae.

Except for the use of the specified light field, the cultivation of algae in accordance with this invention does not require any special cultivating conditions, and can be performed in accordance with conventional cultivating methods for Chlorella, Spirulina, Scenedesmus, or conventional operating methods and conditions used in the cultivation of layer, *Laminaria japonica*, and *Underia pinnatifida*.

Possible methods for providing the specified light field include a method which involves irradiating artificial light rays free from light of wavelengths of not more than 340 nm, preferably not more than 360 nm, and more preferably not more than 380 nm, and desirably containing light of wavelengths of at least 550 nm (in this case, a source of the artificial light rays may emit light having such optical properties, or the light irradiated from such an artificial light source through a suitable filter); a method involving irradiating sunlight through a transparent colorless or colored covering material which substantially inhibits the transmission of light of wavelengths of not more than 340 nm, preferably not more than 360 nm, more preferably not more than 380 nm; and a combination of these two methods.

For example, in the cultivation of algae of the genus Spirulina in accordance with the method of this invention, the above-specified light field is formed on the water surface of a pool or pond under sunlight by covering the entire water surface with a specified covering material to be described hereinbelow, and the cultivation is carried out in such pool or pond. As is conventional, various fertilizers such as nitrogen, potassium (e.g., potassium nitrate) phosphoric acid, acid potassium phosphate, sodium chloride, traces of iron, magnesium are added to the pool or pond, and the water is agitated by blowing air or carbon dioxide into it. The temperature of water is generally kept at about 20° to 30° C., and the illuminance of the light is preferably maintained at at least 5,000 lux. Under these conditions, the cultivation can be performed for 4 to 10 days. The cultivated Spirulina algae can be separated from water in the pond or pool by a customary method such as filtration. Thus, Spirulina algae having good quality, a high protein content and high nutritional value can be obtained in high yields.

In the cultivation of algae of the genus Chlorella in a tank under the irradiation of artificial light rays, the tank is filled with a culture solution containing nitrogen, phosphoric acid and potassium fertilizers and as trace constituents, sodium nitrate, potassium dihydrogen phosphate, magnesium sulfate, calcium chloride, sodium chloride and iron chloride, and the Chlorella algae are added. As a light source, those containing substantially no light of the aforesaid short wavelength region is used, or such light sources as a xenon lamp are used and the light of wavelengths of not more than 340 nm is shut off by means of a spectrograph, an optical filter, etc. Preferably, the cultivation is carried out while maintaining the illuminance of the light at 4000 to 8000 lux, and irradiating the light for a period of 15 to 18 hours a day. The temperature of the cultivation liquor is preferably 25° C.±2° C., and the cultivation liquor is agitated while blowing carbon dioxide under a pressure of 2 to 3 atmospheres into it. As a result, Chlorella algae of very good quality can be efficiently obtained in high yields.

The method of this invention is specifically illustrated below with reference to the cultivation of laver (genus Porphyra such as *P. tenera*) as a typical example.

In the conventional cultivation of laver, a so-called hardening phenomenon occurs frequently by which the leaf portion of the laver grows with a gradual decrease in elasticity until finally the growth is retarded and the entire body of the laver becomes aged. This phenomenon is seen especially in the middle and later stages of the cultivation. This hardening phenomenon causes a marked decrease in the grade of laver on the market, and greatly affects the laver producers.

No clear cause for the hardening phenomenon has been determined, and therefore, no effective measure for its prevention is available. The only practice now performed is to cover the laver culture with Victoria lawn, etc. However, this method of cultivation under the cover of Victoria lawn is not sufficient for preventing the hardening, and it is desired to develop a more effective method for preventing such a hardening phenomenon.

It has now been found that when laver is cultivated in the specified light field in accordance with this invention, hardening is scarcely seen in the harvested laver, and laver of high quality can be obtained, and that the harvested laver has a high quality with superior color, flavor and gloss and the yield increases.

Thus, according to one preferred embodiment of this invention, there is provided a method for cultivating laver which comprises growing the laver under the specified optical conditions at least after the initiation of its cultivation after its spore growing period, preferably from the spore-growing period onward.

Laver is a lower plant belonging to the Division Rhodophyta of the plant kingdom. The practice of cultivating laver somewhat differs from place to place. In Japan, spores are usually collected in the beginning to middle of October, shell spores released from oyster shells are incubated on cultivation nets, and the spores are grown in a spore-growing area until about the middle of November. Then, the cultivation is performed from the middle of November to about March the next year. During the cultivation period, the laver is harvested about 3 to 5 times per net.

The procedure of laver cultivation is briefly shown below.

(1) Spore collection

This is done from the beginning to middle of October. Lavor spores in the shells of shellfish are incubated on cultivation nets in the sea in a plastic bag. The number of nets was 60 per lot.

(2) Growth of spores

This is done from the beginning to about November 10 for 30 to 40 days. The nets to which spores have been incubated are transferred to a spore-growing area of the sea, and the laver spores are grown to a height of 1 to 3 cm. At this time of the year, the sea is usually gentle with weak wind.

(3) Storage (refrigeration)

This is started at the end of October for the purpose of storing the grown laver spores, and sterilizing the nets. The nets with the spores are placed in refrigerators and stored at −20° C. As required, the nets are taken out from the refrigerators and used in cultivation.

(4) Cultivation

This is done from the beginning of November to March the next year. The grown laver spores are cultivated in a cultivation area by a support post method or a floating method.

(5) Harvesting

This is done from the beginning of November to March the next year. A decrease in quality becomes marked in the second to third harvesting. The laver hardens, is without gloss, and is delustered changing from black to light brown.

When the method of this invention is applied to the cultivation of laver, the covering material in accordance with this invention to be described hereinbelow is spread over laver cultivation nets set in a bay or inlet with relatively gentle waves so that the sunlight which does not pass through the covering material may not fall upon the laver cultivation nets.

As another specific example of the method of this invention, the cultivation of ball algae, or *Cladophora sauteri*, is described below.

Since the ball algae are weak to direct sunlight, they are usually cultivated under shade. Under direct sunlight, the ball algae change to white in color at the surface in about 1 to 4 hours, and then further change to yellow, brown, and to black, and finally die. However, when the ball algae are cultivated under shade, their growth is very poor because of the shortage of the quantity of light, and the amount of their growth is only about 0.5 to 1.0 cm in diameter. Thus, the cultivaters desire the development of a cultivating technique which can grow ball algae at high speeds under a large quantity of light while preventing their death.

It has now been found that when ball algae are cultivated in the specified light field, the ball algae do not die even under sunlight, but photosynthesis become vigorous and the growth of the ball algae is promoted, thus affording ball algae having a dark green color and very much improved quality. Thus, their merchandise value increases.

Thus, according to another preferred embodiment of this invention, there is provided a method for cultivating *Cladophora sauteri*, which comprises growing *Cladophora sauteri* in the above-specified light field at least after the alga has become spherical, preferably from the time before it became spherical, and while the individual algal cells are in the state of short fibers.

*Cladophora sauteri* is a lower plant belonging to Division Chlorophyta, and is cultivated throughout the year in fresh water through a cycle consisting of the cultivation of starting algae, the making of the starting algae into spherical shapes (by the palm, an eddy water current, and an automated machine), and the cultivation of the spherical algae.

The cultivation of *Cladophora sauteri* is performed usually in a water tank. When the method of the present invention is to be applied to the cultivation of *Cladophora sauteri*, it is desirable to spread the covering material of this invention over the water tank so as to cover it almost entirely.

A suitable procedure of performing the method of this invention is to cultivate algae under a covering material which substantially inhibits the transmission of light of wavelengths of not more than 340 nm, preferably not more than 360 nm, especially preferably 380 nm, and desirably permits the substantial transmission of light of wavelengths of at least 550 nm, preferably at least 450 nm.

The term "covering material which substantially inhibits the transmission of light of the above-specified wavelength region" denotes not only a covering material which completely inhibits the transmission of the light of the specified wavelength, but also a covering material which permits the transmission of up to 30%, preferably up to 20%, more preferably up to 10%, of the light of the specified wavelength.

The term "covering material which permits the substantial transmission of light of the specified wavelength" denotes not only a covering material which permits the 100% transmission of the light of the specified wavelength, but also a covering material which somewhat inhibits the transmission of the light of the specified wavelength with the consequent decrease of the light transmittance to 50%, preferably 70%, more preferably 90%.

Transmission of the light of wavelengths of from 340 nm to 550 nm may be substantially permitted or substantially inhibited. Generally, it is advantageous that the average transmittance of the light of the above-specified wavelength region is 10 to 95%, preferably 30 to 90%.

According to another aspect of the invention, there is provided a covering material having the aforesaid light-transmitting properties for use in the cultivation of algae.

The material for the covering material of this invention is not particularly restricted so long as it has the aforesaid light-transmitting properties. Usually, the covering material of this invention may be composed of an inorganic or organic film, plate and other shaped article. Typical examples of the inorganic film or plate include a glass plate containing a dye or pigment (Emerald Green), and a glass plate having a plastic film containing an ultraviolet absorber of the types exemplified hereinbelow coated or laminated thereon. Plastic films or plates having an ultraviolet absorber coated thereon or incorporated therein are especially preferred.

Box-like, hollow or foamed articles of synthetic resins containing ultraviolet absorbers can also be used as the covering material of this invention floating on the water surface. In addition to thermoplastic resins to be described hereinbelow, thermosetting resins such as melamine resin, phenol resin, epoxy resin, silicone resin, urea resin, alkyd resin, and allyl phthalate resin can also be used.

Plastic films or plates containing ultraviolet absorbers are especially suitable as the covering material of this invention. These plastic films and plates are described in detail hereinbelow.

Transparent films or plates that can be used in this invention can be produced, for example, by blending an ordinary film-forming thermoplastic resin with a suitable ultraviolet absorber, and shaping the mixture into a film or sheet.

Examples of the film-forming thermoplastic synthetic resins are polyvinyl chloride, polyvinylidene chloride, polyethylene, polypropylene, polystyrene, polyesters, polyamides, polycarbonate, polymethyl methacrylate, acrylate resins, polyvinyl acetate, polyvinyl alcohol, fluorine-containing resins, cellulosic resins, ABS resin, copolymers consisting mainly (preferably at least 50% by weight) of the monomeric units of these polymers, and blends of these polymers or copolymers. From the viewpoint of light resistance, strength and light transmitting property, polyvinyl chloride, polyethylene, polypropylene, fluorine-containing resins, cellulosic resins and polystyrene are preferred.

Ultraviolet absorbers having the ability to substantially inhibit the transmission of light of wavelengths of not more than 340 nm when incorporated into the aforesaid synthetic resins can be selected from a wide range of species according to their ultraviolet absorbing ability, their compatibility with the synthetic resins, etc. Examples of such ultraviolet absorbers are listed below.

Hydroquinone compounds

Hydroquinone and hydroquinone disalicylate.

Salicylic acid compounds

Phenyl salicylate and p-octylphenyl salicylate.

Benzophenone compounds

2-Hydroxy-4-methoxybenzophenone,
2-hydroxy-4-n-octoxybenzophenone,
2-hydroxy-4-methoxy-2-carboxybenzophenone,
2,4-dihydroxybenzophenone,
2,2'-dihydroxy-4,4'-dimethoxybenzophenone,
2-hydroxy-4-benzoyloxybenzophenone,
2,2'-hydroxy-4-methoxybenzophenone,
2-hydroxy-4-methoxy-5-sulfonebenzophenone,
2,2',4,4'-tetrahydroxybenzophenone,
2,2'-hydroxy-4,4'-dimethoxy-5-sodiumsulfobenzophenone,
4-dodecyloxy-2-hydroxybenzophenone, and
2-hydroxy-5-chlorobenzophenone.

Benzotriazole compounds 2-(2'-hydroxy-5'-methylphenyl)benzotriazole,
2-(2'-hydroxy-5'-methylphenyl)-5-butylcarbonate benzotriazole,
2-(2'-hydroxy-5'-methylphenyl)-5,6-dichlorobenzotriazole,
2-(2'-hydroxy-5'-methylphenyl)-5-ethylsulfonebenzotriazole,
2-(2'-hydroxy-5'-tert-butylphenyl)-5-chlorobenzotriazole,
2-(2'-hydroxy-5'-tert-butylphenyl)benzotriazole,
2-(2'-hydroxy-5'-aminophenyl)benzotriazole,
2-(2'-hydroxy-3',5'-dimethylphenyl)benzotriazole,
2-(2'-hydroxy-3',5'-dimethylphenyl)-5-methoxybenzotriazole,
2-(2'-methyl-4'-hydroxyphenyl)benzotriazole,
2-(2'-stearyloxy-3',5'-dimethylphenyl)-5-methylbenzotriazole,
2-(2'-hydroxy-5'-phenylcarbonate)benzotriazole ethyl ester,
2-(2'-hydroxy-3'-methyl-5'-tert-butylphenyl) benzotriazole,
2-(2'-hydroxy-3',5'-di-tert-butylphenyl)-5-chlorobenzotriazole,
2-(2'-hydroxy-5'-methoxyphenyl)benzotriazole,
2-(2'-hydroxy-5'-phenylphenyl)-5-chlorobenzotriazole,
2-(2'-hydroxy-5'-dichlorohexylphenyl)benzotriazole,
2-(2'-hydroxy-4',5'-dimethylphenyl)-5-carboxylic acid benzotriazole butyl ester,
2-(2'-hydroxy-3',5'-dichlorophenyl)benzotriazole,
2-(2'-hydroxy-4',5'-dichloro)benzotriazole,
2-(2'-hydroxy-3',5'-dimethylphenyl)-5-ethylsulfonebenzotriazole,
2-(2'-hydroxy-5'-phenylphenyl)benzotriazole,
2-(2'-hydroxy-4'-octoxyphenyl)benzotriazole,
2-(2'-hydroxy-5'-methoxyphenyl)-5-methylbenzotriazole,
2-(2'-hydroxy-5'-methylphenyl)-5-carboxylic acid ester benzotriazole,
2-(2'-acetoxy-5'-methylphenyl)benzotriazole,
2-(2'-hydroxy-3',5'-di-tert.butylphenyl)-5-chlorobenzotriazole,
2-(2'-hydroxy-3'-tert-butyl-5'-methylphenyl)-5-chlorobenzotriazole,
2-(2'-hydroxy-3'-tert-butyl-5'-methylphenyl)-5,6-dichlorobenzotriazole, and
2-(2'-hydroxy-3',5'-di-tert-butylphenyl)-4,4-dichlorobenzotriazole Among these ultraviolet absorbers, the benzophenone compounds and the benzotriazole compounds are preferred. Among the benzophenone compounds, 2,3'-dihydro-xy-4,4'-dimethoxybenzophenone, 2,2'-dihydroxy-4-methoxybenzophenone and 2,2',4,4'-tetrahydroxybenzophenone are especially preferred. On the other hand, especially preferred benzotriazole compounds are 2-(2'-hydroxy-5'-methylphenyl)benzotriazole, 2-(2'-hydroxy-5'-methylphenyl)-5,6-dichlorobenzotriazole, 2-(2'-hydroxy-5'-tert-butylphenyl)benzotriazole, 2-(2'-hydroxy-3'-methyl-5'-tert-butylphenyl)benzotriazole, 2-(2'-hydroxy-3',5'-di-tert-butylphenyl)-5-chloro-benzotriazole, 2-(2'-hydroxy-5'-phenylphenyl)-5-chlorobenzotriazole, 2-(2'-hydroxy-3',5'-di-tert-butylphenyl)-5-chlorobenzotriazole, 2-(2'-hydroxy-5'-octoxyphenyl)benzotriazole, 2-(2'-hydroxy-3'-tert-butyl-5'-methylphenyl)-5-chlorobenzotriazole, and 2-(2'-hydroxy-3'-tert-butyl-5'-methylphenyl)-5,6-dichlorobenzotriazole.

Especially preferred ultraviolet absorbers are benzotriazole derivatives of the following formula

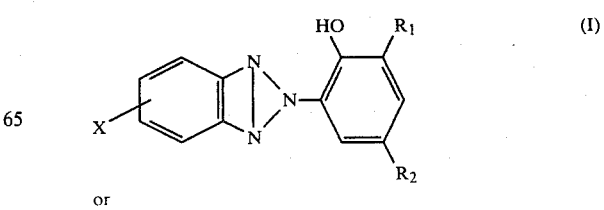

or

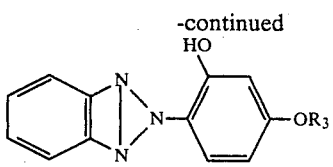
(II)

wherein $R_1$ and $R_2$ are identical or different and each represents a lower alkyl group or an aryl group, especially a phenyl group, $R_1$ preferably representing a branched lower alkyl group having not more than 5 carbon atoms or a phenyl group, $R_3$ represents an alkyl group containing at least 6 carbon atoms, especially 8 to 10 carbon atoms, and X represents a hydrogen atom or a halogen atom, especially a chlorine atom.

The amount of the ultraviolet absorber can be varied over a wide range depending upon the type of the ultraviolet absorber, the type of the synthetic resin used, the thickness of the film or plate, etc. It has been found that in order to achieve the substantial inhibition of the transmission of ultraviolet rays having a wavelength of not more than 340 nm, preferably not more than 360 nm, especially preferably not more than 380 nm, the following relation is preferably established between the amount of the ultraviolet absorber and the thickness of the resulting film or plate.

$$15 \leqq AB \leqq 600,$$

preferably $$20 \leqq AB \leqq 400$$

in which A is the amount (PHR) of the ultraviolet absorber, and B is the thickness (microns) of the film or plate.

PHR denotes the number of parts by weight per 100 parts by weight of the synthetic resin.

The suitable amount (A) of the ultraviolet absorber is generally 0.001 to 5 PHR, and in the case of a film, preferably 0.1 to 5.0 PHR.

In addition to the ultraviolet absorber, the synthetic resin used in this invention may contain small amounts of other conventional additives such as plasticizers, lubricants, antioxidants, light stabilizers, antistatic agents, moisture-proofing agents, heat stabilizers, dyes, pigments, and agents for preventing adhesion of unwanted algae, shellfish, and other fouling materials.

The plastic film, plate or other shaped articles can be produced by various known methods, for example a calendering method, a melt-extrusion method such as inflation, a press method, a solution casting method, or an injection molding method. To prevent the deterioration of the physical properties of the film, another resin may be coated on it, or another film may be laminated on it.

The thickness of the film, plate and other shaped article can be varied widely. Generally, to achieve the objects of this invention, the suitable thickness is 15 to 5,000 microns, especially 20 to 3,000 microns. As required, the film or plate may be laminated on another plastic film or sheet or a glass sheet in order to reinforce it. The plastic film or sheet, especially the former, may also be reinforced with reinforcing fibers such as glass fibers, wire meshes, or a net-like fibrous structure.

As required, to prevent the adhesion of shellfish, algae and fouling materials to the covering material of this invention which reduces its transparency, the covering material of this invention may be surface-treated with a chemical for inhibiting the adhesion of shellfish and algae, or a synthetic resin containing such a chemical may be coated or laminated on it.

In forming the specified optical field using the covering material of this invention, it is not necessary to shield the entire cultivation system of algae from ultraviolet rays of the specified wavelength region. Usually, it is sufficient to cover the cultivation system such that it substantially inhibits the transmission of the light of the aforesaid wavelength region which may be present in irradiating light (e.g., direct sunlight) falling at least upon the algal bodies in the cultivation system.

Usually, direct sunlight and indirect scattered light exist as the light to be irradiated on algae in their cultivation under sunlight. In the method of this invention, it is at least necessary to protect the algae from the direct sunlight.

Various methods of covering algae with the covering material of this invention according, for example, to the cultivation environment and the stage of growth are available. For example, a frame is built up over the water surface of a cultivating area for algae (e.g., pool, pond, lake, inlet, bay), and the covering material is stretched over the frame. Or the covering material is stretched on the water surface in a floating manner. Or supporting posts are provided under the water, and the covering material is stretched over these posts. Combinations of these methods can also be employed.

As is clear from Examples to be given below, the method of this invention can promote algal growth and afford increased yields. It has the advantage that algae having superior quality for example, protein content, flavor, softness, appearance can be easily obtained.

The following Examples further illustrate the present invention.

EXAMPLE A

Production of films:

(1) Polyvinyl chloride (100 parts by weight), 45 parts by weight of dioctyl phthalate (plasticizer), 1.5 parts by weight of dibutyltin maleate (heat stabilizer), 1.0 part by weight of zinc stearate (heat stabilizer), 0.1 part by weight of sorbitan monolaurate (anti-clouding agent), and 1.5 parts by weight of 2-(2'-hydroxy-3',5'-di-tert-butylphenyl)-5-chlorobenzotriazole (ultraviolet absorber) were thoroughly mixed. The mixture was melt-extruded at 200° C. by an extruder to form a transparent film having a thickness of 0.1 mm. This film is designated as "film No. 1", and will be used as a covering material in the following Examples.

(2) A transparent film having a thickness of 0.1 mm was produced by repeating the procedure described in (1) above except that the ultraviolet absorber was changed to 1.4 parts by weight of 2-(2'-hydroxy-5'-methylphenyl)benzotriazole. The film is designated "film No. 2".

(3) A yellow film having a thickness of 0.1 mm was produced by the same procedure as described in (1) above except that the amount of the 2-(2'-hydroxy-3',5'-di-tert-butylphenyl)-5-chlorobenzotriazole was changed to 0.6 part by weight, and 0.5 part by weight of 2,2'-dihydroxy-3-methoxybenzophenone as an additional ultraviolet absorber and 1.2 parts by weight of SYMULER FAST YELLOW 8GTF (made by Dainippon Ink & Chemicals, Co., Ltd.) as a yellow pigment were added. The film is designated as "film No. 3".

(4) A violet film having a thickness of 0.1 mm was produced by the same procedure as described in (1) above except that 0.03 part by weight of MX-460 (made by Dainichi Seika Co., Ltd.) as a blue pigment and 0.3 part by weight MX-4155 (made by Dainichi Seika Co., Ltd.) as a red pigment were added.

(5) For comparison, a polyvinyl chloride film ("NOBI ACE", made by Mitsubishi Monsanto Chemical Co., Ltd.; thickness 0.1 mm), marketed agricultural covering material, was provided. This film is designated as "film No. 5".

The light transmission curves at different wavelengths of these films Nos. 1 to 5 are shown in FIG. 1 of the accompanying drawings.

EXAMPLE 1 AND COMPARATIVE EXAMPLE 1

Two constant-temperature water tanks with one side being a glass plate were provided. The glass surfaces of the tanks were completely covered with films Nos. 1 and 5, respectively.

300 ml. of a cultivation liquor prepared by adding 0.1% of potassium nitrate and 0.01% of sodium citrate to an aqueous solution having the composition of the Allen-Arnon culture medium was placed into each of two 500 ml. cl cultivation bottles. *Anacystis nidulance* (Division Cyanophyta, Class Cyanophyceae, Order Chroococcales, Family Chroococcaceae, Genus Analystis) was put into the bottles in the concentrations indicated in Table 1 as absorbances in the row of "0" elapsed time.

The bottles were dipped in the constant-temperature water tanks, and the temperature of water in the constant-temperature water tanks was adjusted to 30°±1° C. Air was blown into each of the cultivation bottles at a rate of 100 ml/min. Light was irradiated onto the glass surface of each water tank by using "Toshiba Yoko Lamp ®" (made by Toshiba Denzai Co., Ltd.) as a light source. The lamp was lighted for 16 hours and then turned off for 8 hours, and this cycle was repeated for 4 days. The illuminance of the light at the surface of each bottle was about 3,000 lux. The amount of light of wavelengths of not more than 380 nm at the surface of the cultivation bottle in the water tank covered with film No. 1 was 0, and the amount of light of wavelengths of not more than 380 nm at the surface of the cultivation bottle in the water tank covered with film No. 5 was 200 μW/cm².

Every 24 hours, 5 ml of the cultivation liquor was sampled from each bottle, and the growth rate of Anacystis nidulance was determined by the following method. The sampled liquor was centrifuged at 2500 rpm for 10 minutes, and the supernatant liquid was removed. 5 to 10 ml of anhydrous methanol was added to the resulting solid layer to dissolve chlorophyll so that the concentration of chlorophyll became optical for measurement of absorbance by a spectrophotometer. The absorbance of this solution at 665 nm (the maximum absorption $\lambda_{max}$ of chlorophyll-a) was measured by a spectrophotometer.

The growth rate (%) was calculated in accordance with the following equation.

$$\text{Growth rate (\%)} = \left\{ \frac{\text{Absorbance of the cultivation liquor covered with film No. 1}}{\text{Absorbance of the cultivation liquor covered with film No. 5}} - 1 \right\} \times 100$$

Table 1

| Time elapsed (days) | Absorbance at 665 nm | | Growth rate (%) |
|---|---|---|---|
| | Example 1 (film No. 1) | Comparative Example 1 (film No. 5) | |
| 0 | 0.004 | 0.004 | 0 |
| 1 | 0.009 | 0.008 | 13 |
| 2 | 0.022 | 0.018 | 22 |
| 3 | 0.052 | 0.039 | 33 |
| 4 | 0.120 | 0.099 | 21 |

It is seen from Table 1 that Example 1 showed a far high rate of growth than Comparative Example 1. As a result of visual observation with unaided eyes, a difference in color ascribable to the difference in the rate of growth of algae is clearly seen between Example 1 and Comparative Example 1 after a lapse of 1 day, and this difference increased with time.

While by conventional techniques, much efforts are required to increase the growth of algae of the genus Anacystis by 10%, it is surprising that the method of this invention showed an effect of increasing the growth by about 10 to 30%.

EXAMPLE 2 AND COMPARATIVE EXAMPLE 2

A cultivation liquor was prepared by adding 1,000 ml of pure water to 5 g of potassium nitrate, 0.1 g of potassium hydrogen phosphate, 0.05 g of magnesium sulfate heptahydrate and 10 drops of a 0.1% aqueous solution of ammonium iron citrate (the medium of Cambridge Culture Collection). Two 500 ml. beakers were each charged with 250 ml of the resulting cultivation liquor. *Microcystis aeruginosa* (Division Cyanophyta, Class Cyanophyceae, Order Chroococcales, Family Chroococcaceae, Genus Microcystis) was placed into the beakers in a concentration corresponding to an absorbance at 500 nm of 0.5850. The temperature of the liquor in the beakers was adjusted to 15° to 25° C. by using a constant-temperature water tank. Cultivation was performed by irradiating light from a marketed glow fluorescent lamp covered with film No. 1 onto one of the beakers, and light from a marketed glow fluorescent lamp covered with film No. 5 onto the other beaker. The illuminance at the surface of the cultivation liquor in each beaker was 1,600 lux, and the irradiation was performed continuously.

The cultivation liquor was periodically sampled, and the absorbance at 500 nm was measured. The growth rate and the growth index for each irradiation time were calculated in accordance with the following equations. The results are shown in Table 2.

$$\text{Growth rate (\%)} = \frac{\text{Absorbance of the cultivation liquor after irradiation}}{0.5850} - 1 \times 100$$

$$\text{Growth index} = \frac{\text{Growth rate under covering with film No. 1}}{\text{Growth rate under covering with film No. 5}} \times 100$$

Table 2

| Irradiation time (hours) | Example 2 Film No. 1 | | Comparative Example 2 Film No. 5 | |
|---|---|---|---|---|
| | Growth rate (%) | Growth index | Growth rate (%) | Growth index |
| 0 | 0 | — | 0 | — |
| 24 | 101 | 110 | 92 | 100 |
| 72 | 221 | 110 | 201 | 100 |

EXAMPLE 3 AND COMPARATIVE EXAMPLE 3

Two 5-liter beakers were each charged with 3 liters of a culture liquor having the composition of the medium of Cambridge Culture Collection (same as that used in Example 2), and Microcystis aeruginosa was put into each of the beaker in a concentration corresponding to an absorbance at 500 nm of 0.5850. The beakers were nearly completely covered with film No. 1 and Film No. 5, respectively. Air was blown into each of the beaker at a rate of 3 liters/min. The beakers were arranged side by side in a well-sunlit outdoor place on a clear day in the beginning of August, and the cultivation of Microcystis aeruginosa was performed under sunlight from 11 o'clock in the morning to 5 o'clock in the afternoon. The beakers were water-cooled so that the temperature of the culture liquor in each beaker was maintained at 25° C.

After the cultivation, the growth index was calculated in the same way as in Example 2. The results are shown in Table 3.

Table 3

| | Example 3 | Comparative Example 3 |
|---|---|---|
| Covering film | No. 1 | No. 5 |
| Quantity of light (*) | | |
| 380 nm–650 nm | 70,000–20,00 lux | 70,000–20,000 lux |
| 290 nm–380 nm | 0 μW/cm² | 2500–700 μW/cm² |
| Growth index | 155 | 100 |

(*)The quantity of light was the value measured on the surface of the culture liquor in the beakers.

EXAMPLE 4 AND COMPARATIVE EXAMPLR 4

Two liters of sea water from Toyama Bay, Japan were placed in each of two 3-liter beakers. *Spirulina platensis* (Division Cyanophyceae, Class Cyanophyceae, Order Nostocales, Family Oscillatoriaceae, Genus Spirulina) was placed in each beaker in a concentration corresponding to an absorbance at 500 nm of 0.2040. The beakers were completely covered with films Nos. 1 and 2, respectively. Air was blown into each of the beakers at a rate of 2 liters/min. On fine days in the beginning of August, the beakers were arranged side by side for 48 hours in a well-sunlit outdoor place, and cultivation was performed under sunlight. The beakers were water-cooled so that the temperature of the liquor within the beakers was kept at 21° to 23° C.

After the cultivation, the growth indices were calculated in the same way as in Example 2. The results are shown in Table 4.

Table 4

| | Example 4 | Comparative Example 4 |
|---|---|---|
| Covering film No. | 1 | 5 |
| Growth index | 158 | 100 |

EXAMPLES 5 AND 6 AND COMPARATIVE EXAMPLE 5

Cultivation nets (each having a size of about 120 cm × about 18 meters) to which spores of laver (genus Porphyra Agardh such as P. teners) were attached in the middle of October were fixed horizontal in an area of spore-growing in the sea with gentle waves by means of supporting posts usually made of bamboo. Thus, the spores of the laver were grown. During the period of growing the laver spores (for about 30 to 40 days), film No. 1 or No. 2 was stretched at a position about 10 to 50 cm above the sea water level at full tide so as to completely cover the entire cultivation nets. Thus, the sunlight arrived at the nets after passage through the covering film.

After the spore growing, the nets were transferred to an area for cultivation in the sea, and set in the same way as above to perform the cultivation of lavor. The method of cultivation includes a support post method and a floating method. Whichever method is used, the way of stretching the film is the same as in the spore growing period. In this Example, the post support method is mainly shown. In the case of the post support method, the difference in sea level between the time of full tide and the time of low tide was about 2 meters. Thus, the cultivation nets were set at a position above 30 to 40 cm below the intermediate level between the full tide and low tide, and the nets were moved up and down according to the growing condition of the laver and the weather condition.

The film No. 1 or No. 2 was stretched at a position about 10 to about 50 cm above the sea level at full tide, and the position was changed according to the weather and other conditions.

The film No. 1 or No. 2 may also be stretched on the sea water surface or below it. In this case, it is preferred to stretch the film at a position about 10 to 100 cm above the cultivation net.

In the case of the floating method, the cultivation nets were suspended by buoys so that they were located a predetermined space (20 to 50 cm) below the sea surface. In this case, the film may be stretched on the sea water surface or under the water surface.

During the cultivation for long periods of time, diatoms and other algae living in the sea, salts, dust, sand and other fouling materials adhered to the net. It was necessary to remove them occasionally. Small holes were provided in the film so as to remove rain waters and sea water on the film.

The cultivation was performed by the conventional method except that the film was stretched over the net as described hereinabove. The results are shown in Table 5.

Harvesting was performed three times from each net until the end of December.

Table 5

| Run | Examined area | Harvest (number per net) (a) | Softness in eating (b) | Appearance of laver | |
|---|---|---|---|---|---|
| | | | | Blackness (c) | Gloss (d) |
| Example 5 | Area covered with film No. 1 | 3000 | 7 | 5 | 8 |
| Example 6 | Area covered with film | 2700 | 3 | 4 | 2 |

Table 5-continued

| Run | Examined area | Harvest (number per net) (a) | Softness in eating (b) | Appearance of laver Blackness (c) | Gloss (d) |
|---|---|---|---|---|---|
| Comparative Example 5 | No. 2 Not covered | 2,050 | 0 | 0 | 0 |

The items shown in Table 2 are explained as follows:
(a) Amount of harvest

The number of laver sheets, 19.1 cm × 17.6 cm in size, which were harvested until the end of December.
(b) Evaluation of the softness of laver to the palate Organoreptically evaluated by a panel of ten specialists. The result is expressed by the number of panelists who gave the best rating to the laver tested.
(c) Evaluation of the blackness of the laver Organoreptically evaluated by a panel of ten specialists. The result is expressed by the number of panelists who gave the best rating to the laver tested.
(d) Evaluation of gloss Organoreptically evaluated by a panel of ten specialists. The result is expressed by the number of panelists who gave the best rating to the laver tested.

As is clearly seen from Table 5, the amount of harvest was far larger in the areas covered with films Nos. 1 and 2 than in the area not covered with these films, and the quality of laver harvested from these covered areas was very much improved as seen from the softness, color and gloss of the product. This effect was especially outstanding in the area covered with film No. 1, and the laver harvested from this area could sell at a higher price.

Similar results were obtained when the cultivation was performed from December to March using refrigerated nets. Surprisingly, the period of cultivation of the laver could be prolonged by about two weeks as compared with that in the non-covered area.

Similar results were obtained when the position of stretching the film No. 1 was always under the sea water surface (the floating method), or when it was above or below the sea water surface by the effect of tide (the support post method).

Thus, the method of the present invention could substantially completely prevent the hardening of laver against which no effective preventive measure had been available.

Furthermore, by the use of films Nos. 1 and 2 in accordance with this invention, the number of laver sheets harvested increased remarkably, and a marked effect was produced in the improvement of laver quality such as its softness to the palate, color, flavor and gloss.

The method of this invention, therefore, contributes greatly to the laver producers.

EXAMPLE 7 AND COMPARATIVE EXAMPLE 6

Films Nos. 1 and 5 were respectively stretched over two pipe houses each having a width of 4.5 m, a length of 20 m and a height of 2.2 m. Two 50-liter water tanks were disposed in each of the houses.

On October 20, each of the water tanks was sterilized with 2 ppm of sodium hypochlorite, and then 30 liters of neutralized sea water (specific gravity 1.014) and as fertilizers, "Organic No. 280" (a trademark for a product of Nitto Chemical Industry Co., Ltd.) in a concentration of 100 g/ton of sea water and "CLEWAT 32" (a trademark for a product of Teikoku Chemical Industry Co., Ltd.) in a concentration of 20 g/ton of sea water were put into each water tank to prepare a culture medium.

Figure 2:
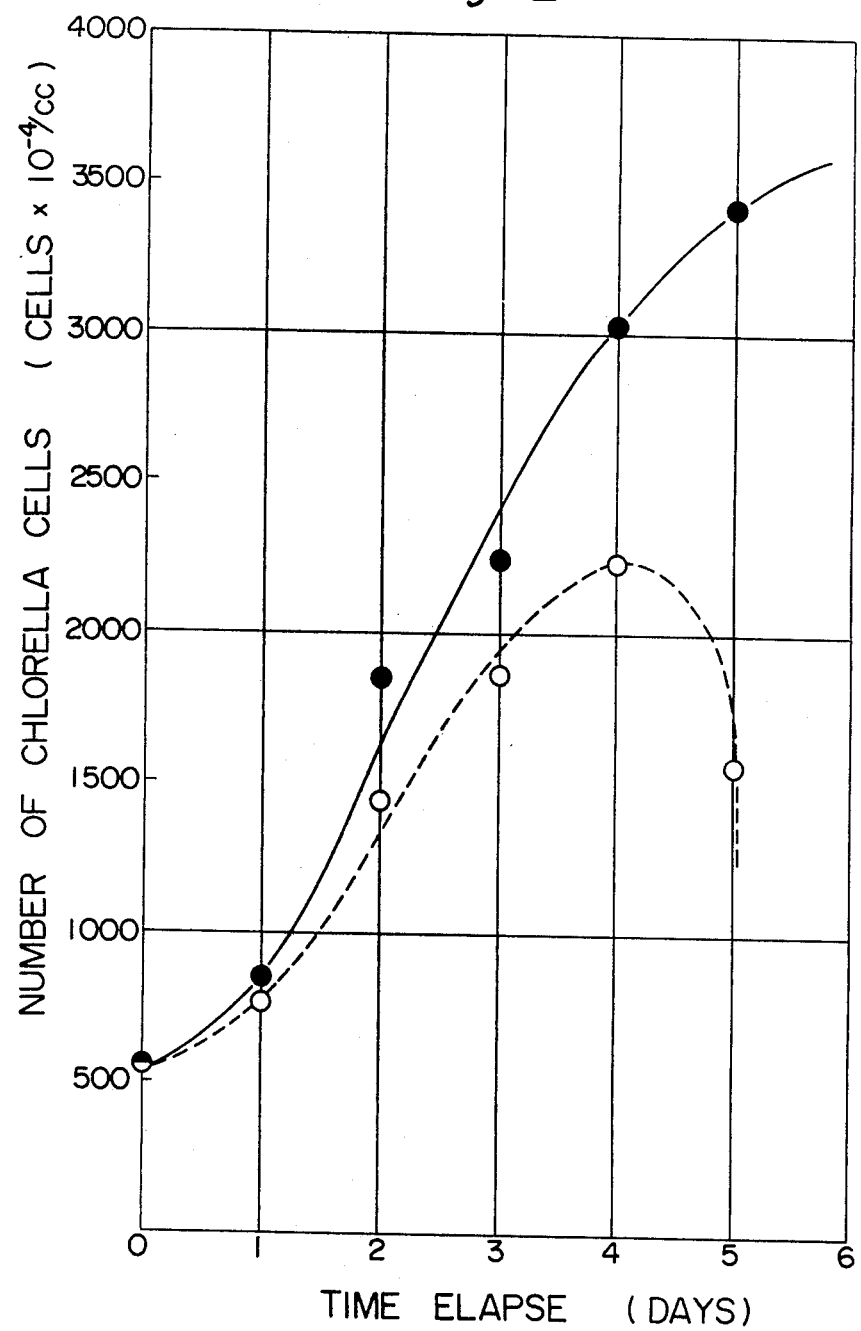

On October 22, *Chlorella vulgaris* (Division Chlorophyta, Class Chlorophyceae, Order Chlorococcales, Family Chlorellaceae, Genus Chlorella) was added so that its concentration in each water tank became 559 cells/cc of culture medium. Air was blown into the water tanks at a rate of 10 liters/min, and the water temperature was maintained at 25° to 20° C. In this manner, the Chlorella algae were grown for 6 days. The results of growth are shown in Table 6 and FIG. 2 of the accompanying drawings.

The number of Chlorella cells was measured by the method described in Hiroshi Tamiya and Atsushi Watanabe, "Methods of Experiments on Algae" (4th edition, published June 20, 1975, Nankodo Press, Tokyo, Japan) using the Thoma's counting chamber.

Table 6

| | Number of Chlorella cells ($\times 10^4$/cc) | | | | | | Growth rate (%) (*) |
|---|---|---|---|---|---|---|---|
| Time | Example 7 (film No. 1) | | | Comparative Example 6 (film No. 5) | | | |
| elapsed (days) | 1st area | 2nd area | Average | 1st area | 2nd area | Average | |
| 0 | 559 | 559 | 559 | 559 | 559 | 559 | 100 |
| 1 | 849 | 837 | 843 | 741 | 793 | 767 | 110 |
| 2 | 1888 | 1792 | 1840 | 1288 | 1600 | 1444 | 127 |
| 3 | 2196 | 2267 | 2232 | 1920 | 1808 | 1864 | 120 |
| 4 | 3216 | 3072 | 3144 | 2104 | 2384 | 2244 | 140 |
| 5 | 3688 | 3168 | 3428 | 1048 | 2080 | 1564 | 220 |

(*) The growth rate is calculated as follows:

$$\text{Growth rate} = \frac{\text{Average in Example 7}}{\text{Average in Comparative example 6}} \times 100$$

The growth rate increased after a lapse of 1 day, and this was clearly seen also by visual examination. After a lapse of 4 days, the growth in Example 7 was vigorous, while the growth in Comparative Example 6 stopped, and the death of the Chlorella cells was remarkable. After a lapse of 5 days, this tendency was strong, and the number of cells in Comparative Example 6 was less than one half of that in Example 7.

EXAMPLE 8 AND COMPARATIVE EXAMPLE 7

Three liters of a culture liquor having the composition of the Bristol culture medium (prepared by adding 0.5 g of sodium nitrate, 0.5 g of potassium dihydrogen phosphate, 0.15 g of magnesium sulfate heptahydrate, 0.05 g of calcium chloride, 0.05 g of sodium chloride and 0.01 g of ferric chloride hexahydrate to 1,000 ml of pure water) were put into each of two 5-liter beakers. In the same way as in Example 7, *Chlorella pyrenoidosa* (300 million cells/cc) was put into each of the beakers. The beakers were almost completely covered with films Nos. 1 and 5, respectively. Air was blown into each of the beakers at a rate of 3 liters/min.

On fine days in the beginning of August, the two beakers were arranged side by side in a well-sunlit outdoor place for 48 hours, and the Chlorella cells were cultivated under sunlight. The beakers were water-cooled so as to maintain the temperature of the liquid at about 23° C.

The number of cells after cultivation was measured by the same method as in Example 7, and the rate of growth and the growth index were calculated in accordance with the following equations. The results are shown in Table 7.

$$\text{Growth rate (\%)} = \frac{\text{Number of Chlorella cells before the experiment}}{\text{Number of Chlorella cells after the experiment}} \times 100$$

$$\text{Growth index} = \frac{\text{Growth rate in Example 8}}{\text{Growth rate in Comparative Example 7}} \times 100$$

Table 7

|  | Comparative Example 7 | Example 8 |
|---|---|---|
| Films used | No. 5 | No. 1 |
| Number of Chlorella cells before the experiment (millions/cc) | 300 | 300 |
| Number of Chlorella cells after the experiment (millions/cc) | 550 | 900 |
| Growth rate (%) | 183 | 300 |
| Growth index | 100 | 163 |

The quantity of sunlight at the water surface during the above experiment is shown in Table 8.

Table 8

| Time of measurement (o'clock) | 14 | 15 | 16 |
|---|---|---|---|
| Quantity of visible light (cal/cm$^2$ · min.) (400–700 nm) | 0.35 | 0.33 | 0.13 |
| Quantity of ultraviolet light ($\mu$W/cm$^2$) (300–400 nm) | 2800 | 2300 | 1000 |

EXAMPLES 9 TO 11 AND COMPARATIVE EXAMPLES 8 TO 10

Forty liters of pure water taken from the upstream of a river was put into each of six 50-liter tanks, and 1.0 g of *Cladophora sauteri* (Division Chlorophyta, Class Chlorophyceae, Order Cladophorales, Family Cladophoraceae, Genus Cladophora) (weighed after centrifugal separation at 1,500 rpm for 5 minutes) was put into each of the water tanks. Four tanks were entirely covered with films Nos. 1, 3, 4 and 5, respectively, and the remaining two tanks were not covered. These tanks were disposed in a well-sunlit outdoor place. The temperature of water was maintained at 25°±1° C. by a thermostat, and air was blown into each of the water tanks at a rate of 4 liters/min. The cultivation of *Cladophora sauteri* was continued for 3 days under the sunlight. One non-covered tank was disposed under a tree to avoid direct irradiation of the sunlight.

The results are shown in Table 9.

Table 9

|  | Example 9 Film No. 1 | Example 10 Film No. 3 | Example 11 Film No. 4 | Comparative Example 8 Film No. 5 | Comparative Example 9 non-covered | Comparative Example 10 non-covered (under a tree) |
|---|---|---|---|---|---|---|
| Weight (grams) of *Cladophora sauteri* At the outset of the experiment | 1.0 | 1.0 | 1.0 | 1.0 | 1.0 | 1.0 |
| After a lapse of 3 days | 1.6 | 1.8 | 1.3 | — | — | 1.1 |
| Observation | Growth was rapid, and the color was deep | Growth was very rapid | The Color of the alga was very deep and became dark green. | After a lapse of 1 to 2 days, the alga became whitish, then changed to yellow, brown and finally to black, and died. |  | Growth was scarcely seen noted. |

EXAMPLES 12 TO 18 AND COMPARATIVE EXAMPLES 11 TO 16

Algae A to F shown in Table 10 were each cultivated for 7 days under sunlight while covering the cultivation areas with Film No. 1, No. 2 or No. 5.

After the cultivation, the culture liquor was sampled in an amount of 1 to 3 ml according to the concentrations of the algae, and centrifuged at 4,000 rpm for 20 to 40 minutes. The volume or weight of the solid obtained were measured. The volume or weight of the solid from the area covered with film No. 1 was taken as 100, and the volume or weight of the solid from the area covered with film No. 2 or No. 5 was converted on this basis and made a growth index. The results are shown in Table 11.

Table 10

| Designation | Division of the plant kingdom | Class | Order | Family | Genus | Species | Growth culture medium |
|---|---|---|---|---|---|---|---|
| A | Cyanophyta | Cyanophyceae | Nostocales | Nostocaceae | Anabaena | *A. spiroides* | Allen-Arnon |
| B | Rhodophyta | Protoflorideophyceae | Porphyridiales | Porphyridiaceae | Porphyridium | *P. Cruentum* | Eyster-Brown Hood |
| C | Chrysophyta | Bacillariophyceae | Centrales | Discacea | Coscinodiscus | *C. asteromphalus* | Sudo |
| D | " | Bacillariophyceae | Pennales | Naviculaceae | Navicula | *N. radiosa* | Fogg |
| E | Chlorophyta | Chlorophy- | Volvocales | Chlamydomo- | Chlamydo- | *C. nivalis* | Sagger- |

Table 10-continued

| Designation | Division of the plant kingdom | Class | Order | Family | Genus | Species | Growth culture medium |
|---|---|---|---|---|---|---|---|
| F | " | ceae Chlorophyceae | Chlorococcales | nadaceae Coelastraceae | monas Scenedesmus | S. quardicauda | Granick Pascher |

Table 11

| Genus | Run | Covering film No. | Growth index |
|---|---|---|---|
| Anabaena | Example 12 | 1 | 100 |
| | Example 13 | 2 | 96 |
| | Comparative Example 11 | 5 | 77 |
| Porphyridium | Example 14 | 1 | 100 |
| | Comparative Example 12 | 5 | 84 |
| Coscinodiscus | Example 15 | 1 | 100 |
| | Comparative Example 13 | 5 | 69 |
| Navicula | Example 16 | 1 | 100 |
| | Comparative Example 14 | 5 | 78 |
| Chlamydomonas | Example 17 | 1 | 100 |
| | Comparative Example 15 | 5 | 82 |
| Scenedesmus | Example 18 | 1 | 100 |
| | Comparative Example 16 | 5 | 76 |

Cultivation under covering with film No. 1 or 2 was also performed in the same way as in the above Examples with regard to algae belonging to Genus Nostoc, Family Nostocaceae, Order Nostocales, Class Cyanophyceae, Division Cyanophyta; Genus Skeletonema, Family Discaceae, Order Centrales, Class Bacillariophyceae, Division Chrysophyta; Genus Chaetocerus, Family Biddulphiaceae, Order Centrales, Class Bacillariophyceae, Division Chrysophyta; Genus Exuviaella, Family Prorocentraceae, Order Thecatales, Class Dinophyceae, Division Pyrrhophyta; Genus Amphidinium, Family Gymnodiniaceae, Order Peridiniales, Class Dinophyceae, Division Pyrrhophyta; and Genus Laminaria, Family Laminariaceae, Order Laminariales, Class Heterogeneratae, and Genus Undaria, Family Alariaceae, Order Laminariales, Class Heterogeneratae, both of Division Phaeophyta.

Similar growth promoting effects as in the above Examples were obtained.

EXAMPLE 19 AND COMPARATIVE EXAMPLE 17

The procedure of Example 1 was repeated except that a black fluorescent lamp FL20S-BLB (a product of Tokyo Shibaura Denki K.K.) was used as a light source in addition to the Toshiba Yoko Lamp ® so as to cause the irriadiating light in the near ultraviolet region (about 300 to 400 nm) to become as close to sunlight as possible.

The Toshiba Yoko Lamp ® was operated in a cyclo consisting of 16 hours' lighting and 8 hours' turning off, whereas the black fluorescent lamp was lighted continuously for 24 days.

The illuminance of light at the surface of each cultivation bottle was 6,000 lux when both of these lamps were lighted. At this time, the quantity of light of a wavelength region of not more than 380 nm was 0 at the surface of the cultivation bottle in the water tank covered with film No. 1, and about 2,500 $\mu W/cm^2$ at the surface of the cultivation bottle in the tank covered with film No. 5.

The temperature of the inside of the water tanks was maintained at $27° \pm 1°$ C.

The rate of growth of Anacystis nidulance was determined in the same way as in Example 1, and the results are shown in Table 12.

Table 12

| Elapsed time (days) | Absorbance at 665 nm (log $I_0/I_o$) | | Rate of growth |
|---|---|---|---|
| | Example 19 | Comparative Example 17 | |
| 0 | 0.004 | 0.004 | 100 |
| 1 | 0.010 | 0.008 | 125 |
| 2 | 0.030 | 0.009 | 333 |
| 3 | 0.124 | 0.012 | 1.033 |
| 4 | 0.254 | 0.020 | 1.270 |
| 5 | 0.355 | 0.031 | 1.145 |

It is seen from Table 12 that the growth in Example 19 was promoted by more than 10 times that in Comparative Example 17.

The cell volume of Anacystis nidulance was measured in the following manner. 2.5 cc of the culture liquid was sampled, and centrifuged at 2800 rpm for 20 minutes. The packed volume of the sedimented cells was measured in accordance with the method described in "Method of Experiments on Algae", edited by Hiroshi Tamiya, pages 186 to 187 (4th impression, published by Nankodo on June 30, 1975). As a result, on the fifth day of cultivation, the packed volume of the cells of Anacystis nidulance per ml of the culture liquid was 1.24 $\mu l$ in Example 19, and 0.20 $\mu l$ in Comparative Example 17. The grown cells of Anacystis nidulance in Example 19 and Comparative Example 17 were examined by a microscope. It was found that the cells in Example 19 were normal and of high quality, but the cells in Comparative Example 17 were generally small and showed an irregular malformed state with several small cells gathering without being able to separate from each other.

EXAMPLE 20 AND COMPARATIVE EXAMPLE 18

Two 5-liter glass bottles were covered with films Nos. 1 and 5, respectively. A glow fluorescent lamp was set so that the light illuminated on the surface of each glass bottle had an illuminance of 3,000 lux. Each of the glass bottles was charged with 3.5 liters of the Provasoli-Pinter culture medium, and 200 cells/cc of Gymnodinium breve (Division Pyrrhophyta, Subclass Dinophycidae, Order Peridiniales, Family Gymnodiniaceae, Genus Gymnodinium) were added. The culture medium was agitated while blowing air into it at a rate of 300 ml/min. The temperature of the culture medium was maintained at 20° to 25° C., and a cultivation test was performed. The number of cells of breve species was determined in the same way as in Example 7 after irradiating light from the glow fluorescent lamp continuously for 12 days. The results are shown in Table 13.

Table 13

|  | Example 20 (I) | Comparative Example 18* (II) | Degree of promotion of growth (I/II) |
| --- | --- | --- | --- |
| Covering film | No. 1 | No. 5 |  |
| Number of cells per cc |  |  |  |
| Before irradiation | 200 | 200 | 1 |
| After irradiation | 35,000 | 25 | 1400 |

*In Comparative Example 18, the number of the cells did not increase, but with the advance of irradiation, tended to decrease and die.

It is clearly seen from Table 13 that in Example 20, the growth of the breve species was remarkable, but in Comparative Example 18, the cells of the breve species gradually died.

What is claimed is:

1. A method for cultivating an alga, which comprises growing the alga in a light field substantially free from light of wavelengths of not more than 340 nm.

2. The method of claim 1 wherein said light field is substantially free from light of wavelengths of not more than 360 nm.

3. The method of claim 1 wherein the light field is substantially free from light of wavelengths of not more than 380 nm.

4. The method of any one of claims 1 to 3 wherein the alga is cultivated in a light field in which light of wavelengths of at least 550 nm is present.

5. The method of claim 1 wherein the cultivation is carried out by passing said light field through a covering material which substantially inhibits the transmission of light of wavelengths of not more than 380 nm and substantially permits transmission of light of wavelengths of at least 550 nm.

6. The method of claim 1 wherein the alga belongs to Division Cyanophyta, Division Rhodophyta, Division Chrysophyta, Division Phaeophyta, or Division Chlorophyta.

7. The method of claim 1 wherein the alga belongs to the genera Anacystis, Microcystis, Spirulina, Anabaena, Nostoc, Porphyridium, Porphyra, Gelidium, Coscinodiscus, Skeletonema, Chaetocerus, Navicula, Exuviaella, Amphidinium, Gymnodinium, Nemocystus, Laminaria, Undaria, Chlamydomonas, Chlorella, Scenedesmus, or Cladophora.

8. The method of any one of claims 1, 2, 3 or 5 wherein the source of the light field is sunlight.

9. The method of any one of claims 1, 2, 3 or 5 wherein the source of the light field is artificial light.

* * * * *

UNITED STATES PATENT AND TRADEMARK OFFICE
CERTIFICATE OF CORRECTION

PATENT NO. : 4,235,043
DATED : November 25, 1980
INVENTOR(S) : Harawawa, et al.

It is certified that error appears in the above—identified patent and that said Letters Patent is hereby corrected as shown below:

ASSIGNEE:

Delete "Kabashiki" and insert --Kabushiki--.

Signed and Sealed this

Third Day of March 1981

[SEAL]

*Attest:*

RENE D. TEGTMEYER

*Attesting Officer*    *Acting Commissioner of Patents and Trademarks*